(12) United States Patent
Petersen

(10) Patent No.: US 6,991,642 B2
(45) Date of Patent: Jan. 31, 2006

(54) WIRE AND LOCK MECHANISM

(75) Inventor: Scott R. Petersen, Brooklyn Park, MN (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 10/352,420

(22) Filed: Jan. 28, 2003

(65) Prior Publication Data

US 2003/0176887 A1 Sep. 18, 2003

Related U.S. Application Data

(63) Continuation of application No. 09/800,182, filed on Mar. 6, 2001, now Pat. No. 6,537,295.

(51) Int. Cl.
 *A61M 29/00* (2006.01)

(52) U.S. Cl. ...................................... 606/200

(58) Field of Classification Search ................. 606/159, 606/191, 198, 200
See application file for complete search history.

(56) References Cited

U.S. PATENT DOCUMENTS

| | | | | |
|---|---|---|---|---|
| 3,472,230 A | 10/1969 | Fogarty | ...................... | 128/328 |
| 3,592,186 A | 7/1971 | Oster | .......................... | 128/2 R |
| 3,683,904 A | 8/1972 | Forster | ...................... | 128/127 |
| 3,889,657 A | 6/1975 | Baumgarten | .................... | 128/2 |
| 3,952,747 A | 4/1976 | Kimmell, Jr. | ............ | 128/303 R |
| 3,996,938 A | 12/1976 | Clark, III | ..................... | 128/348 |
| 4,046,150 A | 9/1977 | Schwartz et al. | ............ | 128/328 |
| 4,425,908 A | 1/1984 | Simon | ............................. | 128/1 |
| 4,447,227 A | 5/1984 | Kotsanis | ...................... | 604/95 |

(Continued)

FOREIGN PATENT DOCUMENTS

| | | | |
|---|---|---|---|
| DE | 28 21 048 | 7/1980 | |
| DE | 34 17 738 | | |
| DE | 40 30 998 A1 | 10/1990 | |
| EP | 0 200 688 | 11/1986 | |
| EP | 0 293 605 A1 | 12/1988 | |
| EP | 0 411 118 A1 | 2/1991 | |
| EP | 0 427 429 A2 | 5/1991 | |
| EP | 0 437 121 B1 | 7/1991 | |
| EP | 0 472 334 A1 | 2/1992 | |
| EP | 0 472 368 A2 | 2/1992 | 11/1985 |

(Continued)

OTHER PUBLICATIONS

"Atherosclerotic Disease of the Aortic Arch as a Risk Factor of Recurrent Ischemic Stroke," *The New England Journal of Medicine*, pp. 1216–1221 (May 1996).

"Endovascular Grafts, Stents Drive Interventional Radiology Growth," *Cardiovascular Device Update*, 2(3):1–12 (Mar. 1996).

"Protruding Atheromas in the Thoracic Aortic and Systemic Embolization," pp. 423–427 American College of Physicians (1991).

(Continued)

Primary Examiner—Julian W. Woo
Assistant Examiner—Charles H. Sam
(74) Attorney, Agent, or Firm—Crompton, Seager & Tufte LLC

(57) ABSTRACT

Methods and devices for delivering and/or retrieving a filter fixed to a guidewire disposed within a blood vessel are disclosed. A system in accordance with the present invention comprises, an outer shaft having a proximal end, distal end and a wall defining an outer shaft lumen. The system also includes a stop mechanism disposed within the outer shaft lumen. The stop mechanism is preferably configured such that relative axial movement between the guidewire and the outer shaft may be selectively precluded.

14 Claims, 14 Drawing Sheets

U.S. PATENT DOCUMENTS

| | | |
|---|---|---|
| 4,580,568 A | 4/1986 | Gianturco .................... 128/345 |
| 4,590,938 A | 5/1986 | Segura et al. ................ 128/328 |
| 4,619,246 A | 10/1986 | Molgaard-Nielsen et al. .. 128/1 |
| 4,631,052 A | 12/1986 | Kensey ......................... 604/22 |
| 4,643,184 A | 2/1987 | Mobin-Uddin ............. 128/303 |
| 4,650,466 A | 3/1987 | Luther .......................... 604/95 |
| 4,662,885 A | 5/1987 | DiPisa, Jr. .................... 623/12 |
| 4,705,517 A | 11/1987 | DiPisa, Jr. .................... 623/12 |
| 4,706,671 A | 11/1987 | Weinrib ..................... 128/348.1 |
| 4,723,549 A | 2/1988 | Wholey et al. ............. 128/344 |
| 4,728,319 A | 3/1988 | Masch .......................... 604/22 |
| 4,733,665 A | 3/1988 | Palmaz ....................... 128/343 |
| 4,790,812 A | 12/1988 | Hawkins, Jr. et al. ........ 604/22 |
| 4,790,813 A | 12/1988 | Kensey ......................... 604/22 |
| 4,794,928 A | 1/1989 | Kletschka .................. 128/344 |
| 4,794,931 A | 1/1989 | Yock ...................... 128/660.03 |
| 4,800,882 A | 1/1989 | Gianturco .................... 128/343 |
| 4,807,626 A | 2/1989 | McGirr ......................... 128/328 |
| 4,842,579 A | 6/1989 | Shiber .......................... 606/22 |
| 4,857,045 A | 8/1989 | Rydell .......................... 604/22 |
| 4,857,046 A | 8/1989 | Stevens et al. ............... 604/22 |
| 4,867,157 A | 9/1989 | McGurk-Burleson et al. ........................ 128/305 |
| 4,873,978 A | 10/1989 | Ginsburg .................... 128/345 |
| 4,898,575 A | 2/1990 | Fischell et al. ............... 604/22 |
| 4,907,336 A | 3/1990 | Gianturco .................... 29/515 |
| 4,921,478 A | 5/1990 | Solano et al. ................. 604/53 |
| 4,921,484 A | 5/1990 | Hillstead .................... 604/104 |
| 4,926,858 A | 5/1990 | Gifford, III et al. ........ 606/159 |
| 4,950,277 A | 8/1990 | Farr ............................ 606/159 |
| 4,955,895 A | 9/1990 | Sugiyama et al. .......... 606/194 |
| 4,957,482 A | 9/1990 | Shiber .......................... 604/22 |
| 4,969,891 A | 11/1990 | Gewertz ..................... 606/200 |
| 4,979,951 A | 12/1990 | Simpson ..................... 606/159 |
| 4,986,807 A | 1/1991 | Farr ............................ 604/22 |
| 4,998,539 A | 3/1991 | Delsanti ..................... 128/898 |
| 5,002,560 A | 3/1991 | Machold et al. ............. 606/198 |
| RE33,569 E | 4/1991 | Gifford, III et al. ........ 606/159 |
| 5,007,896 A | 4/1991 | Shiber .......................... 604/22 |
| 5,007,917 A | 4/1991 | Evans ......................... 606/170 |
| 5,011,488 A | 4/1991 | Ginsburg .................... 606/159 |
| 5,019,088 A | 5/1991 | Farr ............................ 606/159 |
| 5,041,126 A | 8/1991 | Gianturco .................... 606/195 |
| 5,053,008 A | 10/1991 | Bajaj ......................... 604/104 |
| 5,053,044 A | 10/1991 | Mueller et al. ............. 606/159 |
| 5,071,407 A | 12/1991 | Termin et al. .............. 604/104 |
| 5,071,425 A | 12/1991 | Gifford, III et al. ........ 606/159 |
| 5,085,662 A | 2/1992 | Willard ....................... 606/159 |
| 5,087,265 A | 2/1992 | Summers ..................... 606/159 |
| 5,100,423 A | 3/1992 | Fearnot ......................... 606/15 |
| 5,100,424 A | 3/1992 | Jang et al. ................... 606/159 |
| 5,100,425 A | 3/1992 | Fischell et al. ............. 606/159 |
| 5,102,415 A | 4/1992 | Guenther et al. ........... 606/159 |
| 5,104,399 A | 4/1992 | Lazarus ......................... 623/1 |
| 5,108,419 A | 4/1992 | Reger et al. ................. 606/200 |
| 5,133,733 A | 7/1992 | Rasmussen et al. ........ 606/200 |
| 5,135,531 A | 8/1992 | Shiber ........................ 606/159 |
| 5,152,771 A | 10/1992 | Sabbaghian et al. ........ 606/159 |
| 5,152,777 A | 10/1992 | Goldberg et al. ........... 606/200 |
| 5,160,342 A | 11/1992 | Reger et al. ................. 606/200 |
| 5,171,233 A | 12/1992 | Amplatz et al. ............. 604/281 |
| 5,190,546 A | 3/1993 | Jervis ........................... 606/78 |
| 5,195,955 A | 3/1993 | Don Michael ............... 604/22 |
| 5,201,757 A * | 4/1993 | Heyn et al. ................. 606/198 |
| 5,224,953 A | 7/1993 | Morgentaler ............... 606/192 |
| 5,306,286 A | 4/1994 | Stack et al. ................. 606/198 |
| 5,314,444 A | 5/1994 | Gianturco .................... 606/195 |
| 5,314,472 A | 5/1994 | Fontaine ...................... 623/12 |
| 5,318,576 A | 6/1994 | Plassche, Jr. et al. ........ 606/159 |
| 5,329,942 A | 7/1994 | Gunther et al. ............. 128/898 |
| 5,330,484 A | 7/1994 | Gunther ..................... 606/128 |
| 5,330,500 A | 7/1994 | Song .......................... 606/198 |
| 5,350,398 A | 9/1994 | Pavcnik et al. ............. 606/200 |
| 5,354,310 A | 10/1994 | Garnic et al. ............... 606/198 |
| 5,356,423 A | 10/1994 | Tihon et al. ................ 606/194 |
| 5,366,464 A | 11/1994 | Belknap ..................... 606/159 |
| 5,366,473 A | 11/1994 | Winston et al. ............. 606/198 |
| 5,370,657 A | 12/1994 | Irie ............................ 606/200 |
| 5,370,683 A | 12/1994 | Fontaine ....................... 623/1 |
| 5,376,100 A | 12/1994 | Lefebvre ..................... 606/180 |
| 5,383,887 A | 1/1995 | Nadal ........................ 606/200 |
| 5,383,892 A | 1/1995 | Cardon et al. .............. 606/198 |
| 5,383,926 A | 1/1995 | Lock et al. .................... 623/1 |
| 5,387,235 A | 2/1995 | Chuter ......................... 623/1 |
| 5,395,349 A | 3/1995 | Quiachon et al. ........... 604/248 |
| 5,397,345 A | 3/1995 | Lazerus ........................ 623/1 |
| 5,405,377 A | 4/1995 | Cragg .......................... 623/1 |
| 5,409,454 A | 4/1995 | Fischell et al. ............... 604/22 |
| 5,415,630 A | 5/1995 | Gory et al. ................... 604/53 |
| 5,419,774 A | 5/1995 | Willard et al. ................ 604/22 |
| 5,421,832 A | 6/1995 | Lefebvre ...................... 604/53 |
| 5,423,742 A | 6/1995 | Theron ........................ 604/28 |
| 5,423,885 A | 6/1995 | Williams ...................... 623/1 |
| 5,425,765 A | 6/1995 | Tiefenbrun et al. .......... 623/12 |
| 5,443,498 A | 8/1995 | Fontaine ....................... 623/1 |
| 5,449,372 A | 9/1995 | Schmaltz et al. ........... 606/198 |
| 4,842,579 A | 10/1995 | Shiber .......................... 604/22 |
| 5,456,667 A | 10/1995 | Ham et al. .................. 604/107 |
| 5,462,529 A | 10/1995 | Simpson et al. ............. 604/101 |
| 5,476,104 A | 12/1995 | Sheahon ..................... 128/757 |
| 5,484,418 A | 1/1996 | Quiachon et al. ........... 604/167 |
| 5,507,767 A | 4/1996 | Maeda et al. ............... 606/198 |
| 5,512,044 A | 4/1996 | Duer ........................... 604/22 |
| 5,527,354 A | 6/1996 | Fontaine et al. .............. 623/1 |
| 5,536,242 A | 7/1996 | Willard et al. ................ 604/30 |
| 5,540,707 A | 7/1996 | Ressemann et al. ........ 606/159 |
| 5,549,626 A | 8/1996 | Miller et al. ................ 606/200 |
| 5,562,724 A | 10/1996 | Vorwerk et al. ............... 623/1 |
| 5,569,274 A | 10/1996 | Rapacki et al. ............. 606/158 |
| 5,569,275 A | 10/1996 | Kotula et al. ............... 606/159 |
| 5,634,897 A | 6/1997 | Dance et al. ................ 604/35 |
| 5,658,296 A | 8/1997 | Bates et al. ................. 606/127 |
| 5,662,671 A | 9/1997 | Barbut et al. ............... 606/170 |
| 5,669,933 A | 9/1997 | Simon et al. ................ 600/200 |
| 5,681,347 A * | 10/1997 | Cathcart et al. ............ 606/200 |
| 5,695,519 A | 12/1997 | Summers et al. ............ 606/200 |
| 5,709,704 A | 1/1998 | Nott et al. .................. 606/200 |
| 5,720,764 A | 2/1998 | Naderlinger ................ 606/200 |
| 5,728,066 A | 3/1998 | Daneshvar .................... 604/96 |
| 5,746,758 A | 5/1998 | Nordgren et al. ............ 606/159 |
| 5,749,848 A | 5/1998 | Jang et al. ................... 604/53 |
| 5,769,816 A | 6/1998 | Barbut et al. ................ 604/96 |
| 5,779,716 A | 7/1998 | Cano et al. ................. 606/114 |
| 5,792,300 A | 8/1998 | Inderbitzen et al. ... 156/244.13 |
| 5,795,322 A | 8/1998 | Boudewijn ................... 604/22 |
| 5,797,952 A | 8/1998 | Klein ......................... 606/198 |
| 5,800,457 A | 9/1998 | Gelbfish .................... 606/200 |
| 5,800,525 A | 9/1998 | Bachinski et al. ............. 623/1 |
| 5,810,874 A | 9/1998 | Lefebvre .................... 606/200 |
| 5,814,064 A | 9/1998 | Daniel et al. ............... 606/200 |
| 5,817,102 A | 10/1998 | Johnson et al. ............. 606/108 |
| 5,827,324 A | 10/1998 | Cassell et al. .............. 606/200 |
| 5,833,644 A | 11/1998 | Zadno-Azizi et al. .......... 604/52 |
| 5,833,650 A | 11/1998 | Imran ......................... 604/53 |
| 5,846,260 A | 12/1998 | Maahs ....................... 606/200 |
| 5,848,964 A | 12/1998 | Samuels .................... 600/200 |
| 5,876,367 A | 3/1999 | Kaganov et al. .............. 604/8 |
| 5,893,867 A | 4/1999 | Bagaoisan et al. .......... 606/198 |
| 5,895,399 A | 4/1999 | Barbut et al. ............... 606/159 |
| 5,902,263 A | 5/1999 | Patterson et al. ............. 604/22 |
| 5,906,618 A | 5/1999 | Larson, III .................. 606/108 |

| | | | | | | |
|---|---|---|---|---|---|---|
| 5,908,435 A | 6/1999 | Samuels ............... 606/200 | WO | WO 96/19941 | 7/1996 | |
| 5,910,154 A | 6/1999 | Tsugita et al. ........... 606/200 | WO | WO 96/23441 | 8/1996 | |
| 5,911,734 A | 6/1999 | Tsugita et al. ........... 606/200 | WO | WO 96/33677 | 10/1996 | |
| 5,916,193 A | 6/1999 | Stevens et al. ............ 604/53 | WO | WO 97/17100 | 5/1997 | |
| 5,925,016 A | 7/1999 | Chornenky et al. ......... 604/96 | WO | WO 97/27808 | 8/1997 | |
| 5,925,060 A | 7/1999 | Forber ................. 606/191 | WO | WO 97/42879 | 11/1997 | |
| 5,925,062 A | 7/1999 | Purdy ................. 606/200 | WO | WO 98/02084 | 1/1998 | |
| 5,925,063 A | 7/1999 | Khosravi ............... 606/200 | WO | WO 98/02112 | 1/1998 | |
| 5,928,203 A | 7/1999 | Davey et al. ............ 604/247 | WO | WO 98/23322 | 6/1998 | |
| 5,928,218 A | 7/1999 | Gelbfish ............... 604/540 | WO | WO 98/33443 | 8/1998 | |
| 5,934,284 A | 8/1999 | Plaia et al. ............. 128/898 | WO | WO 98/34673 | 8/1998 | |
| 5,935,139 A | 8/1999 | Bates .................. 606/200 | WO | WO 98/36786 | 8/1998 | |
| 5,938,645 A | 8/1999 | Gordon ................. 604/264 | WO | WO 98/38920 | 9/1998 | |
| 5,941,869 A | 8/1999 | Patterson et al. ......... 604/508 | WO | WO 98/38929 | 9/1998 | |
| 5,941,896 A | 8/1999 | Kerr .................. 606/200 | WO | WO 98/39046 | 9/1998 | |
| 5,947,995 A | 9/1999 | Samuels ............... 606/200 | WO | WO 98/39053 | 9/1998 | |
| 5,951,585 A | 9/1999 | Cathcart et al. ......... 606/198 | WO | WO 98/46297 | 10/1998 | |
| 5,954,745 A | 9/1999 | Gertler et al. ........... 606/200 | WO | WO 98/47447 | 10/1998 | |
| 5,976,172 A | 11/1999 | Homsma et al. .......... 606/200 | WO | WO 98/49952 | 11/1998 | |
| 5,989,210 A | 11/1999 | Morris et al. ............ 604/22 | WO | WO 98/50103 | 11/1998 | |
| 5,989,271 A | 11/1999 | Bonnette et al. ......... 606/159 | WO | WO 98/51237 | 11/1998 | |
| 5,989,281 A | 11/1999 | Barbut et al. ........... 606/200 | WO | WO 98/55175 | 12/1998 | |
| 5,993,469 A | 11/1999 | McKenzie et al. ......... 606/159 | WO | WO 99/09895 | 3/1999 | |
| 5,997,557 A | 12/1999 | Barbut et al. ........... 606/159 | WO | WO 99/22673 | 5/1999 | |
| 6,001,118 A * | 12/1999 | Daniel et al. ............ 606/200 | WO | WO 99/23976 | 5/1999 | |
| 6,007,557 A | 12/1999 | Ambrisco et al. ......... 606/200 | WO | WO 99/25252 | 5/1999 | |
| 6,010,522 A | 1/2000 | Barbut et al. ........... 606/200 | WO | WO 99/30766 | 6/1999 | |
| 6,013,085 A | 1/2000 | Howard ................ 606/108 | WO | 0 934 729 | 8/1999 | |
| 6,027,520 A | 2/2000 | Tsugita et al. ........... 606/200 | WO | WO 99/40964 | 8/1999 | |
| 6,042,598 A * | 3/2000 | Tsugita et al. ........... 606/200 | WO | WO 99/42059 | 8/1999 | |
| 6,051,014 A | 4/2000 | Jang ................... 606/200 | WO | WO 99/44510 | 9/1999 | |
| 6,053,932 A | 4/2000 | Daniel et al. ............ 606/200 | WO | WO 99/44542 | 9/1999 | |
| 6,059,814 A | 5/2000 | Ladd .................. 606/200 | WO | WO 99/55236 | 11/1999 | |
| 6,068,645 A | 5/2000 | Tu .................... 606/200 | WO | WO 99/58068 | 11/1999 | |
| 6,086,605 A | 7/2000 | Barbut et al. ........... 606/200 | WO | WO 00/07655 | 2/2000 | |
| 6,129,739 A | 10/2000 | Khosravi ............... 606/200 | WO | WO 00/09054 | 2/2000 | |
| 6,142,987 A | 11/2000 | Tsugita ................ 604/500 | WO | WO 00/16705 | 3/2000 | |
| 6,152,946 A * | 11/2000 | Broome et al. ........... 606/200 | WO | WO 00/49970 | 8/2000 | |
| 6,165,200 A | 12/2000 | Tsugita et al. ........... 606/200 | | | | |
| 6,168,579 B1 | 1/2001 | Tsugita ................ 604/96.01 | | | | |
| 6,171,327 B1 | 1/2001 | Daniel et al. ............ 606/200 | | | | |
| 6,179,851 B1 | 1/2001 | Barbut et al. ........... 606/159 | | | | |
| 6,179,859 B1 | 1/2001 | Bates et al. ............. 606/200 | | | | |
| 6,179,861 B1 | 1/2001 | Khosravi et al. .......... 606/200 | | | | |
| 6,203,561 B1 | 3/2001 | Ramee et al. ........... 606/200 | | | | |
| 6,214,026 B1 | 4/2001 | Lepak et al. ............ 606/200 | | | | |
| 6,277,138 B1 | 8/2001 | Levinson et al. | | | | |
| 2002/0042626 A1 * | 4/2002 | Hanson et al. ........... 606/200 | | | | |

FOREIGN PATENT DOCUMENTS

| | | |
|---|---|---|
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 852 132 A1 | 7/1998 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |

OTHER PUBLICATIONS

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601–604 (Sep. 1983).

Cragg, Andrew et al., "Nonsurgical Placement of Arterial Endoprosthesis: A New Technique Using Nitinol Wire," AJR, pp. 261–263 (Apr. 1983).

Diethrich et al., "Percutaneous Techniques for Endoluminal Carotid Interventions," *J. Endovasc. Surg.*, 3:182–202 (1996).

Fadali, A. Moneim, "A filtering device for the prevention of particulate embolization during the course of cardiac surgery," Surgery, 64(3):634–639 (Sep. 1968).

Haissaguerre et al., "Spontaneous Initiation of Atrial Fibrillation by Ectopic Beats Originating in the Pulmonary Veins," The New England Journal of Medicine, 339(10):659–666 (Sep. 1988).

Jordan, Jr. et al., "Microemboli Detected by Transcranial Doppler Monitoring . . . ," *Cardiovascular Surgery*, 7(1)33–38 (Jan. 1999).

Lesh, "Can Catheter Ablation Cure Atrial Fibrillation?" *ACC Current Journal Review*, pp. 38–40 (Sep./Oct. 1997).

Lund et al., "Long–Term Patentcy of Ductus Arteriosus After Balloon Dilation: an Experimental Study," Laboratory Investigation, 69(4):772–774 (Apr. 1984).

Marache et al., "Percutaneous Transluminal Venous Angioplasty . . . ," *American Heart Journal*, 125(2 Pt 1):362–366 (Feb. 1993).

Mazur et al., "Directional Atherectomy with the Omnicath™: A Unique New Catheter System," Catheterization and Cardiovascular Diagnosis, 31:17–84 (1994).

Moussa, MD, Issaam "Stents Don't Require Systemic Anticoagulation . . . But the Technique (and Results) Must be Optimal," Journal of Invasive Cardiol., 8(E):3E–7E, (1996).

Nakanishi et al., "Catheter Intervention to Venous System Using Expandable Metallic Stents," Rinsho Kyobu Geka, 14(2):English Abstract Only (Apr. 1994).

Onal et al., "Primary Stenting for Complex Atherosclerotic Plaques in Aortic and Iliac Stenoses," Cardiovascular & Interventional Radiology, 21(5):386–392 (1998).

Theron et al., "New Triple Coaxial Catheter System for Carotid Angioplasty with Cerebral Protection," American Journal of Neuroradiology, 11:869–874 (1990).

Tunick et al., "Protruding atherosclerotic plaque in the aortic archo f patients with systemic embolization: A new finding seen by transesophageal echocardiography," *American Heart Journal* 120(3):658–660 (Sep. 1990).

Waksman et al., "Distal Embolization is Common After Directional Atherectomy . . . ," *American Heart Journal*, 129(3):430–435 (1995).

Wholey, Mark H. et al., PTA and Stents in the Treatment of Extracranial Circulation, *The Journal of Invasive Cardiology*, 8(E):25E–30E (1996).

\* cited by examiner

WIRE AND LOCK MECHANISM

This is a continuation of application Ser. No. 09/800,182 filed on Mar. 6, 2001 now U.S. Pat. No. 6,537,295.

FIELD OF THE INVENTION

The present invention relates generally to devices and methods for treating occluded or stenoic blood vessels. More particularly, the present invention relates to devices and methods for providing temporary placement of a filter in a blood vessel during a procedure to remove an occlusion or stenosis.

BACKGROUND OF THE INVENTION

Angioplasty, atherectomy and stent placement, among other procedures, have become well accepted for treatment of coronary lesions. These procedures are often performed as an alternative to coronary bypass. It is also possible, however, that a saphenous vein graft, which is used to bypass coronary lesions, may itself develop a lesion. These lesions may also be treated by minimally invasive procedures such as angioplasty, atherectomy and/or stent placement.

When lesions are treated by these minimally invasive, percutaneous methods, it is possible that particles of plaque, thrombus or other material may break loose from the lesion and drift distally into the smaller coronary arteries. When these minimally invasive methods are performed on native arteries, the plaque or thrombus released during the procedure rarely causes embolization. When these procedures are performed on saphenous vein grafts, however, the incidence of embolism due to the breaking off of plaque or thrombus from the vein graft is substantially greater than from native arteries.

The increased incidence of embolization is believed to be due, at least in part, to the larger diameter of the bypass graft relative to the native artery. The larger diameter of the graft results in a slower blood flow velocity through the graft than the native artery. In addition, the plaque and thrombus of vein grafts is somewhat more fragile than that found in native arteries.

As the difference in embolism associated with treatment of native arteries and vein grafts has been noted, it would be desirable to develop techniques to reduce embolism associated with treatment of vein graft lesions. Additionally, where stent placement or other minimally invasive treatments are performed on the carotid artery, it would be desirable to limit the drift of plaque and thrombus toward the brain.

SUMMARY OF THE INVENTION

The present invention relates generally to devices and methods for treating occluded or stenoic blood vessels. More particularly, the present invention relates to devices and methods for providing temporary placement of a filter in a blood vessel during a procedure to remove an occlusion or stenosis. A system in accordance with the present invention features an outer shaft having a proximal end, a distal end and a wall defining an outer shaft lumen. The system also includes a stop mechanism disposed within the outer shaft lumen. The stop mechanism is preferably configured such that relative axial movement between the guidewire and the outer shaft may be selectively precluded.

In certain implementations of the invention, a proximal guidewire port extends through the wall of the outer shaft for allowing the guidewire to pass through the wall so that it is partially disposed within the shaft lumen. In an advantageous embodiment, the stop mechanism is disposed distally of the proximal guidewire port.

In one aspect of the invention, the stop mechanism is adapted to mechanically engage the guidewire. In an additional aspect of the invention, the stop mechanism is adapted to frictionally engage the guidewire. In yet another aspect of the invention, the stop mechanism is adapted to apply a compressive force to the guidewire.

The stop mechanism may feature a stop member. In certain implementations, the stop member features a ring, and the stop mechanism includes a stop fixed to the guidewire. In one embodiment, the stop member defines an aperture having a inner radial extent, and the stop has an outer radial extent. In an advantageous embodiment, the stop member defines an aperture having a inner radial extent, and the stop has an outer radial extent that is generally greater than the inner radial extent of the aperture defined by the stop member.

In certain implementations of the invention, the stop member features a distal mating surface and the stop features a proximal mating surface. In an advantageous embodiment, the stop and the stop member are configured such that the proximal mating surface of the stop seats against the distal mating surface of the stop member.

In certain implementations, the system features an inner shaft slidingly disposed within the outer shaft lumen. A gripper may be operatively coupled between the inner shaft and the outer shaft. Preferably, the gripper is configured such that relative axial movement between the inner shaft and the outer shaft causes the gripper to grasp the guidewire. In certain implementations, the gripper features a collet.

In certain implementations, the gripper is fixed to the outer shaft. In other implementations, the gripper is fixed to the inner shaft.

DETAILED DESCRIPTION OF THE INVENTION

The following detailed description should be read with reference to the drawings, in which like elements in different drawings are numbered in like fashion. The drawings which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives that may be utilized.

Figure 1:
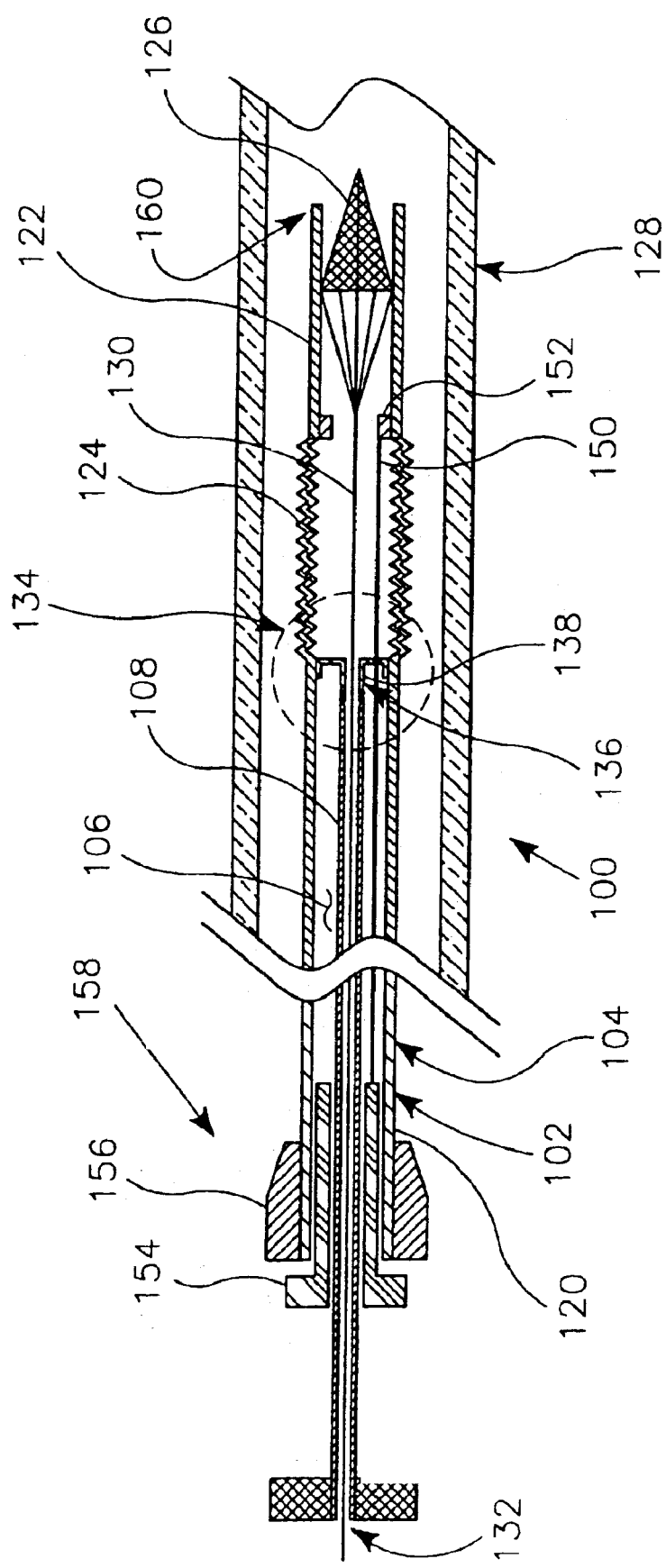
FIG. 1 is a partial cross-sectional view of a filter manipulating system in accordance with an exemplary embodiment of the present invention.

FIG. 1 is a partial cross-sectional view of a filter manipulating system 100 in accordance with an exemplary embodiment of the present invention. Filter manipulating system 100 includes a catheter 102 having an outer shaft 104 defining an outer shaft lumen 106 and an inner shaft 108 that is slidingly disposed within outer shaft lumen 106.

Outer shaft 104 includes a proximal end 158 and a distal end 160. Outer shaft 104 includes a proximal portion 120, a distal portion 122, and a longitudinally collapsible portion 124 disposed between proximal portion 120 and distal portion 122. In the embodiment of FIG. 1 a filter 126 of filter manipulating system 100 is disposed within a portion of outer shaft lumen 106 defined by distal portion 122 of outer shaft 104. In the embodiment of FIG. 1, filter 126 is in a contracted configuration.

Filter manipulating system 100 may preferably be used to deploy filter 126 within a blood vessel 128. Filter manipulating system 100 may also preferably be used to retrieve a filter that is disposed within a blood vessel. In a preferred embodiment, filter 126 assumes an expanded configuration when it is disposed within blood vessel 128 and assumes a contracted configuration when it is disposed within outer shaft lumen 106 of catheter 102.

Filter manipulating system 100 of FIG. 1 includes a guidewire 130 having a distal end that is fixed to filter 126. In the embodiment of FIG. 1, guidewire 130 extends through an inner shaft lumen 132 defined by inner shaft 108. Filter manipulating system 100 also includes a stop mechanism 134 for selectively limiting the longitudinal movement of guidewire 130 relative to proximal portion 120 of outer shaft 104.

In the embodiment of FIG. 1, stop mechanism 134 includes a gripper 136 that is preferably adapted to selectively grasp guidewire 130. In the embodiment of FIG. 1, gripper 136 comprises a collet 138. It is to be appreciated that gripper 136 may comprise various gripping elements without deviating from the spirit and scope of the present invention. Examples of gripping elements that may be suitable in some applications include a set of opposing jaws and a resilient bushing.

Figure 2:
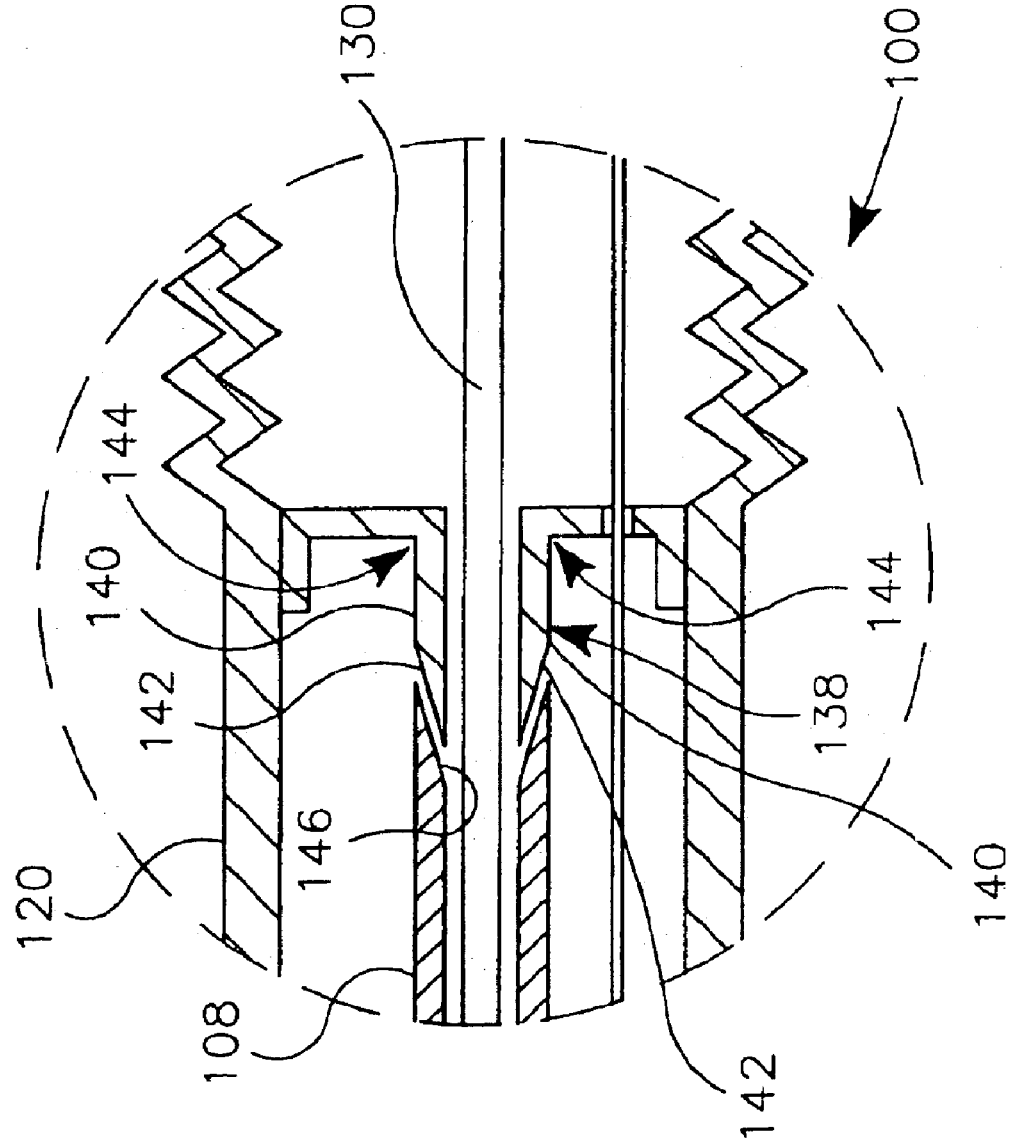
FIG. 2 is an enlarged cross-sectional view of a portion of filter manipulating system of FIG. 1.

FIG. 2 is an enlarged cross-sectional view of a portion of filter manipulating system 100 of FIG. 1. In FIG. 2, collet 138 is shown having an at rest shape. Collet 138 preferably also has a contracted shape in which collet 138 grasps guidewire 130.

In FIG. 2 it may be appreciated that collet 138 includes a plurality of jaws 140, each having a tapered portion 142 and a hinge portion 144. Inner shaft 108 includes a mating taper 146. In a preferred embodiment, relative movement between inner shaft 108 and proximal portion 120 of outer shaft 104 may be used to selectively urge jaws 140 of collet 138 against guidewire 130. In the embodiment of FIG. 2, urging inner shaft 108 distally relative to proximal portion 120 of outer shaft 104 will preferably cause jaws 140 of collet 138 to grasp guidewire 130.

Figure 3:
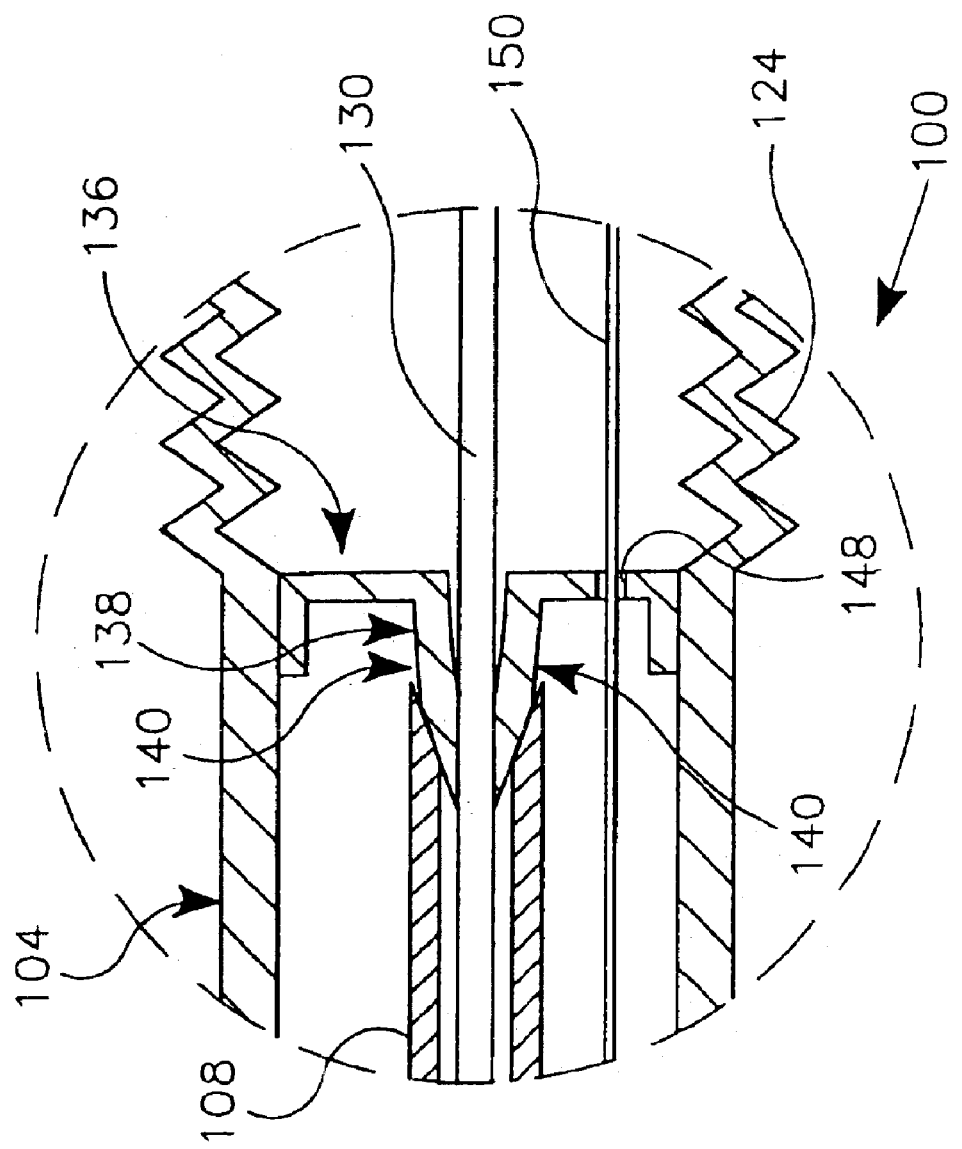
FIG. 3 is an additional enlarged cross-sectional view of the portion of filter manipulating system shown in FIG. 2.

FIG. 3 is an additional enlarged cross-sectional view of the portion of filter manipulating system 100 shown in FIG. 2. In the embodiment of FIG. 3 inner shaft 108 has been moved distally relative to outer shaft 104 and jaws 140 of collet 138 have been urged against guidewire 130. In the embodiment of FIG. 3, collet 138 has been urged into a contracted shape.

In FIG. 3 it may also be appreciated that gripper 136 defines a hole 148. An articulating rod 150 is shown extending through hole 148. Articulating rod 150 may preferably be used to selectively collapse and expand longitudinally collapsible portion 124 of outer shaft 104.

Referring again to FIG. 1, it may be appreciated that a distal end of articulating rod 150 is fixed to a ring 152. Ring 152 is preferably fixed to distal portion 122 of outer shaft 104 distally of longitudinally collapsible portion 124. The proximal end of articulating rod 150 is fixed to a slider 154. Slider 154 is disposed in sliding engagement with a hub 156 that is disposed about a proximal end 158 of outer shaft 104. In a preferred embodiment, slider 154 and articulating rod 150 may be used to selectively collapse and expand longitudinally collapsible portion 124 of outer shaft 104.

Figure 4:
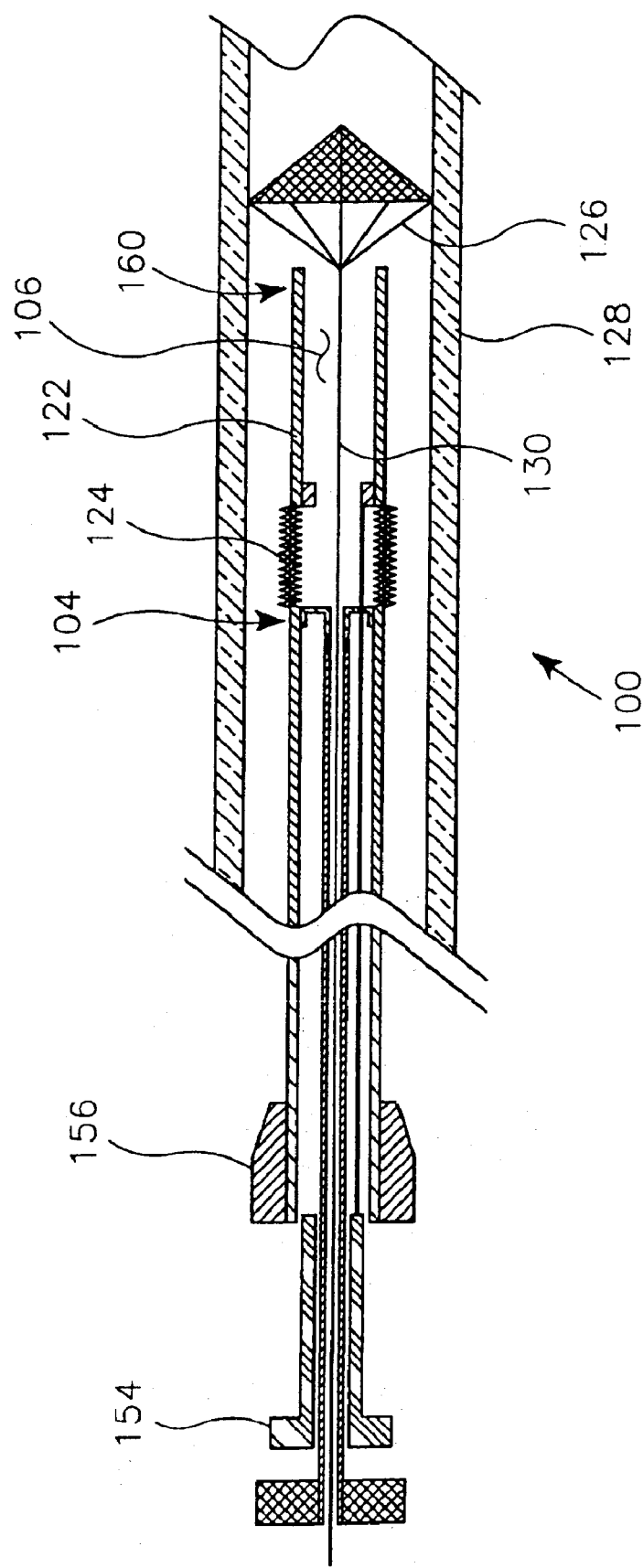
FIG. 4 is an additional partial cross-sectional view of the filter manipulating system of FIG. 1.

FIG. 4 is an additional partial cross-sectional view of the filter manipulating system 100 of FIG. 1. In the embodiment of FIG. 4, longitudinally collapsible portion 124 of outer shaft 104 has been collapsed by urging slider 154 proximally relative to hub 156. In the embodiment of FIG. 4, distal end 160 of outer shaft 104 is located proximally of filter 126 and filter 126 is disposed outside of outer shaft lumen 106. In FIG. 4 it may be appreciated that filter 126 is free to assume an expanded configuration when it is outside of outer shaft lumen 106.

Filter manipulating system 100 of FIG. 4 may preferably be used to retrieve filter 126 from blood vessel 128. For example, filter 126 may be retrieved from blood vessel 128 by selectively grasping guidewire 130 proximate filter 126 and expanding longitudinally collapsible portion 124 by pushing distally on slider 154. By expanding longitudinally collapsible portion 124, distal portion 122 of outer shaft 104 may be urged over filter 126 so that filter 126 is disposed within outer shaft lumen 106. In a preferred embodiment, filter 126 assumes an expanded configuration when it is disposed within blood vessel 128 and assumes a contracted configuration when it is disposed within outer shaft lumen 106 of catheter 102. Filter manipulating system 100 may preferably also be used to deploy a filter within a blood vessel.

Figure 5:
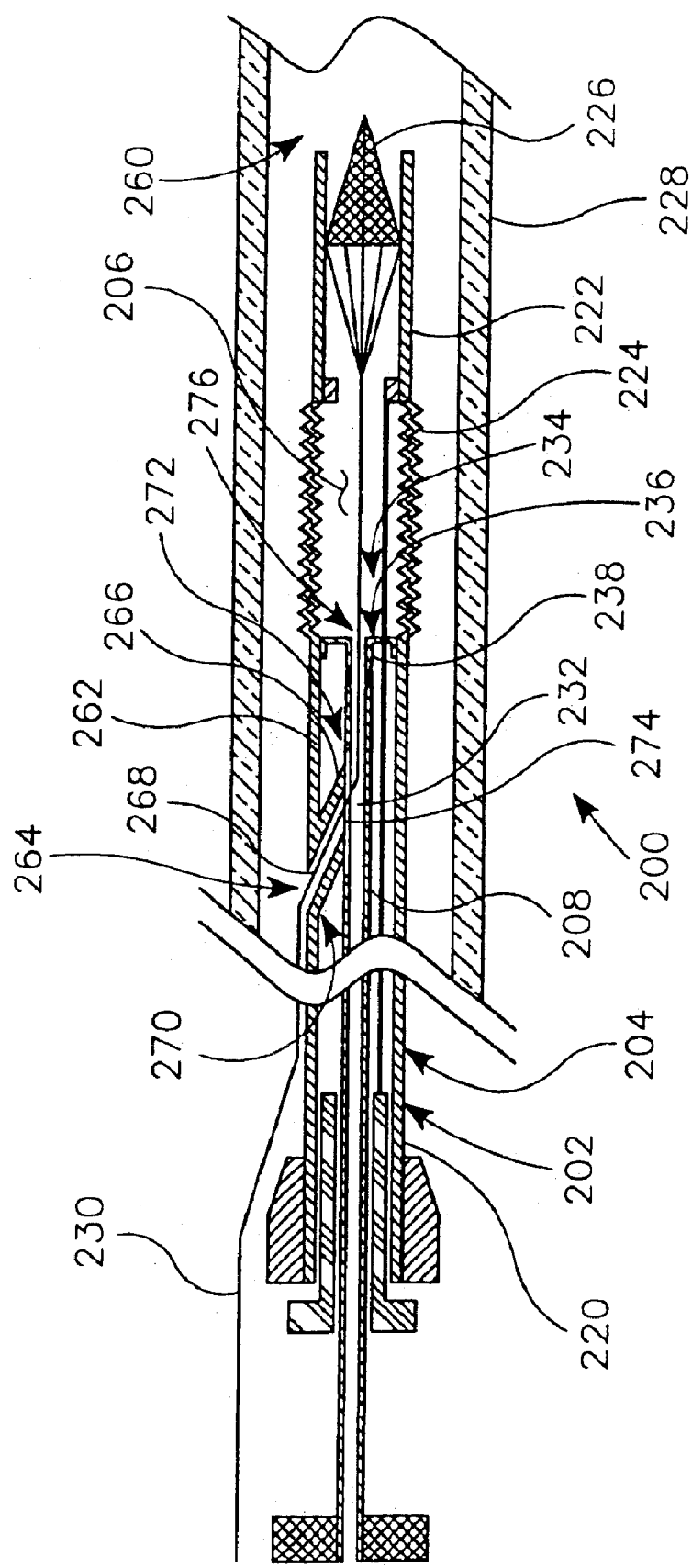
FIG. 5 is a partial cross-sectional view of a filter manipulating system in accordance with an additional exemplary embodiment of the present invention.

FIG. 5 is a partial cross-sectional view of a filter manipulating system 200 in accordance with an additional exemplary embodiment of the present invention. Filter manipulating system 200 comprises a catheter 202 including an outer shaft 204 defining an outer shaft lumen 206. An inner shaft 208 is slidingly disposed within outer shaft lumen 206.

Outer shaft 204 includes a proximal portion 220, a distal portion 222, and a longitudinally collapsible portion 224 disposed between proximal portion 220 and distal portion 222. A wall 262 of proximal portion 220 of outer shaft 204 defines a proximal guidewire port 264. Catheter 202 also includes a tubular member 266 having a first end 270 fixed to wall 262 of proximal portion 220 of outer shaft 204, and a second end 272 disposed within outer shaft lumen 206 proximate inner shaft 208. Tubular member 266 defines a guidewire lumen 268 that is in fluid communication with proximal guidewire port 264.

Various embodiments of proximal guidewire port 264 are possible without deviating from the spirit and scope of the present invention. For example, proximal guidewire port 264 may be defined by wall 262 of proximal portion 220 of outer shaft 204. By way of a second example, proximal guidewire port 264 may be defined by first end 270 of tubular member 266.

In FIG. 5, it may be appreciated that inner shaft 208 of catheter 202 defines an inner shaft lumen 232. A wall of inner shaft 208 defines an aperture 274 that is in fluid communication with inner shaft lumen 232. In FIG. 5, a guidewire 230 is shown extending through proximal guidewire port 264, guidewire lumen 268, aperture 274, and a portion of inner shaft lumen 232.

Filter manipulating system 200 includes a stop mechanism 234 for selectively limiting the longitudinal movement of guidewire 230 relative to proximal portion 220 of outer shaft 204. In the embodiment of FIG. 5, stop mechanism 234 includes a gripper 236 that is preferably adapted to selectively grasp guidewire 230. In the embodiment of FIG. 5, gripper 236 comprises a collet 238. Collet 238 preferably defines a distal guidewire port 276. In FIG. 5, guidewire 230 is shown extending through distal guidewire port 276, a portion of inner shaft lumen 232, aperture 274, guidewire lumen 268, and proximal guidewire port 264.

In the embodiment of FIG. 5, distal guidewire port 276 is disposed proximally of a distal end 260 of outer shaft 204, and proximal guidewire port 264 is disposed proximally of distal guidewire port 276. In FIG. 5, it may be appreciated that distal guidewire port 276 and proximal guidewire port 264 are separated by a longitudinal distance. In a preferred embodiment, the longitudinal distance between proximal guidewire port 264 and distal guidewire port 276 is less than about 55 centimeters. In a particularly preferred embodiment, the longitudinal distance between proximal guidewire port 264 and distal guidewire port 276 is less than about 45 centimeters. In an especially preferred embodiment, the longitudinal distance between proximal guidewire port 264 and distal guidewire port 276 is less than about 35 centimeters.

In the embodiment of FIG. 5 a filter 226 of filter manipulating system 200 is disposed within a portion of outer shaft lumen 206 defined by distal portion 222 of outer shaft 204. In the embodiment of FIG. 5, filter 226 is in a contracted configuration. Catheter 202 of filter manipulating system 200 may preferably be used to deploy filter 226 within a blood vessel 228. Filter 226 may be deployed, for example, by grasping guidewire 230 proximate filter 226 and contracting longitudinally collapsible portion 224. This may cause distal portion 222 of outer shaft 204 to be drawn away from filter 226 so that filter 226 is disposed outside of outer shaft lumen 206. In a preferred embodiment, filter 226 assumes an expanded configuration when it is disposed outside of outer shaft lumen 206 and assumes a contracted configuration when it is disposed within outer shaft lumen 206 of catheter 202. Filter manipulating system 200 may also preferably be used to retrieve a filter that is disposed within a blood vessel.

Figure 6:
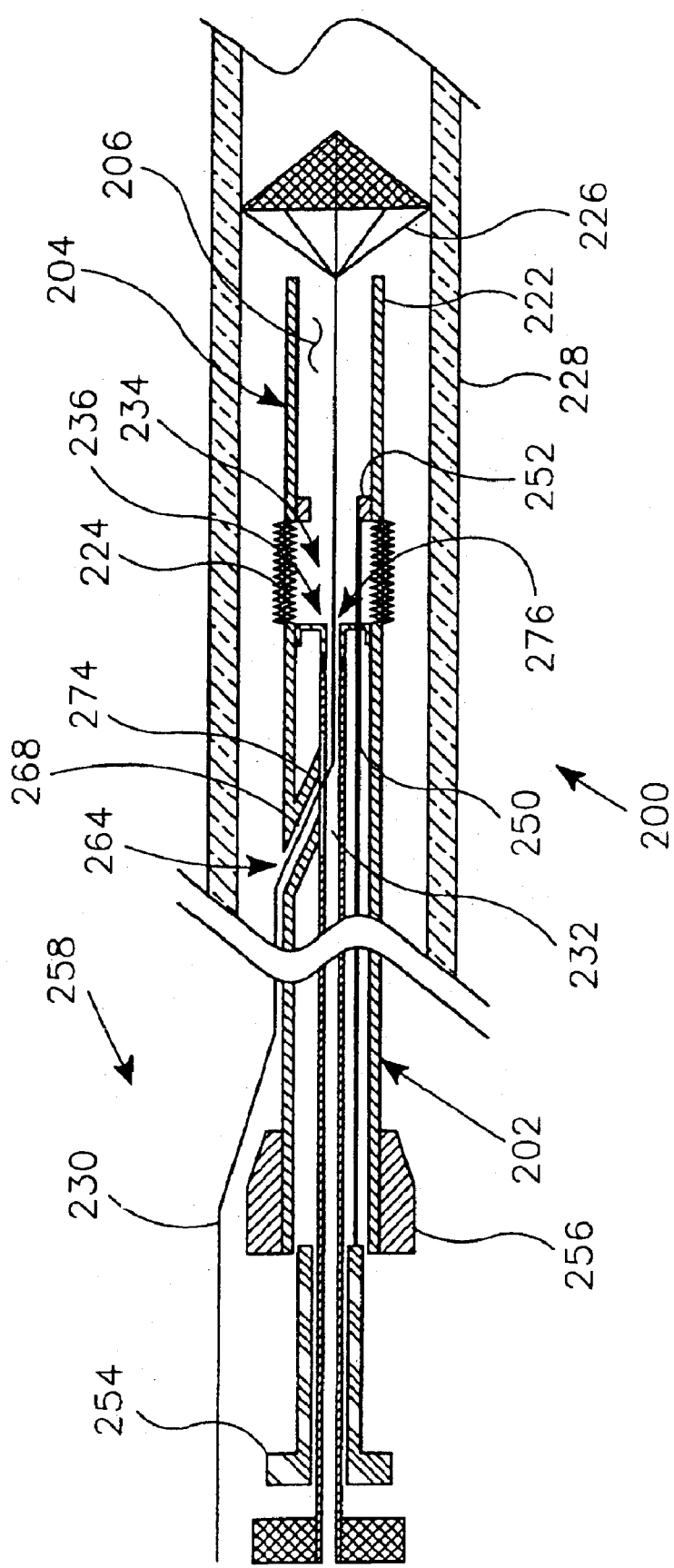
FIG. 6 is an additional partial cross-sectional view of the filter manipulating system of FIG. 5.

FIG. 6 is an additional partial cross-sectional view of the filter manipulating system 200 of FIG. 5. In the embodiment of FIG. 6, filter 226 is disposed within blood vessel 228. Filter 226 may be retrieved, for example, by grasping guidewire 230 with gripper 236 and expanding longitudinally collapsible portion 224 of outer shaft 204. In a preferred embodiment, filter 226 assumes an expanded configuration when it is disposed within blood vessel 228 and assumes a contracted configuration when it is disposed within outer shaft lumen 206 of catheter 202.

In FIG. 6, it may be appreciated that an articulating rod 250 is disposed within outer shaft lumen 206 defined by outer shaft 204. A distal end of articulating rod 250 is fixed to a ring 252. Ring 252 is preferably fixed to distal portion 222 of outer shaft 204 distally of longitudinally collapsible portion 224. The proximal end of articulating rod 250 is fixed to a slider 254. Slider 254 is disposed in sliding engagement with a hub 256 that is disposed about a proximal end 258 of outer shaft 204. In a preferred embodiment, slider 254 and articulating rod 250 may be used to selectively collapse longitudinally collapsible portion 224 of outer shaft 204.

A distal end of a guidewire 230 is shown fixed to filter 226. In the embodiment of FIG. 6, guidewire 230 extends through distal guidewire port 276, a portion of inner shaft lumen 232, aperture 274, guidewire lumen 268, and proximal guidewire port 264. Stop mechanism 234 may preferably be used to selectively grasp guidewire 230 at a location proximate filter 226.

Figure 7:
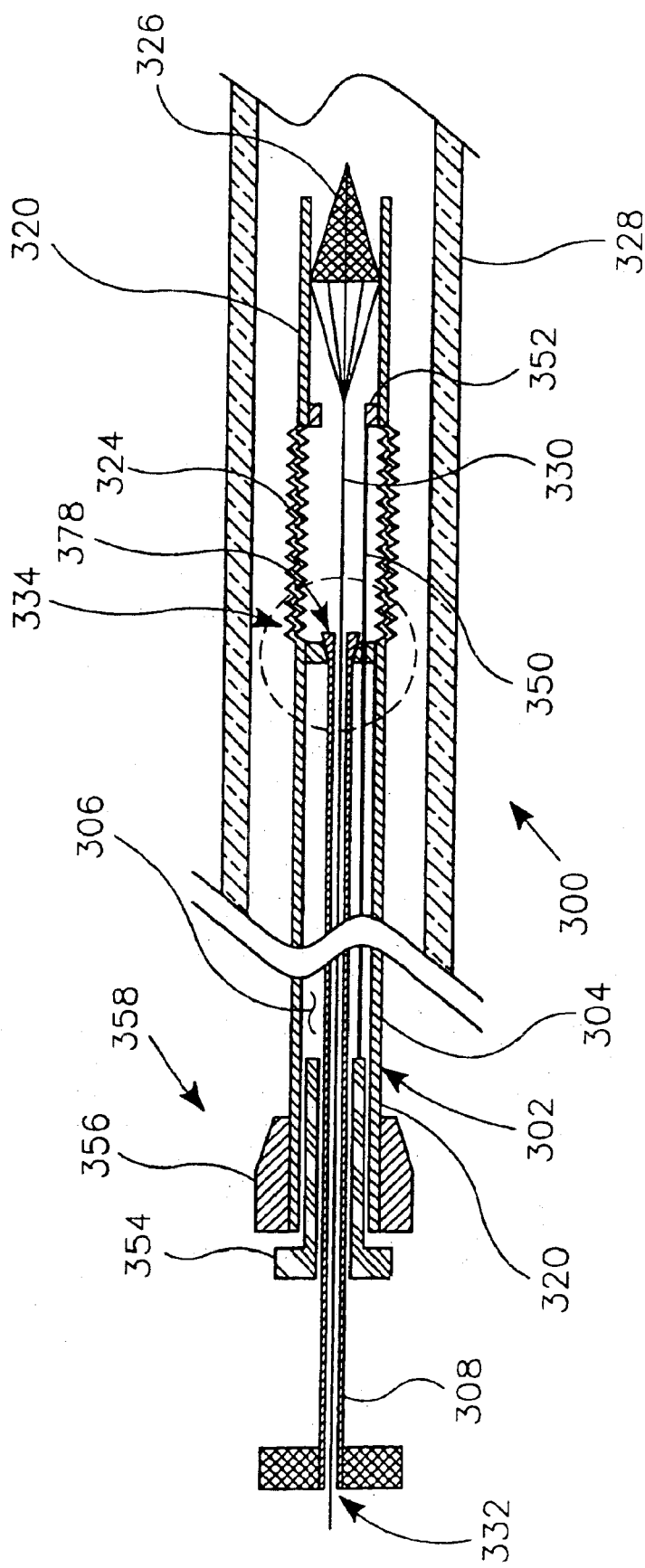
FIG. 7 is a partial cross-sectional view of a filter manipulating system in accordance with an exemplary embodiment of the present invention.

FIG. 7 is a partial cross-sectional view of a filter manipulating system 300 in accordance with an exemplary embodiment of the present invention. Filter manipulating system 300 includes a catheter 302 having an outer shaft 304 defining an outer shaft lumen 306. Outer shaft 304 includes a proximal portion 320, a distal portion 322, and a longitudinally collapsible portion 324 disposed between proximal portion 320 and distal portion 322. In the embodiment of FIG. 7 a filter 326 of filter manipulating system 300 is disposed within a portion of outer shaft lumen 306 defined by distal portion 322 of outer shaft 304. In the embodiment of FIG. 7, filter 326 is in a contracted configuration.

Filter manipulating system 300 may preferably be used to deploy filter 326 within a blood vessel 328. Filter manipulating system 300 may also preferably be used to retrieve a filter that is disposed within a blood vessel. In a preferred embodiment, filter 326 assumes an expanded configuration when it is disposed within blood vessel 328 and assumes a contracted configuration when it is disposed within outer shaft lumen 306 of catheter 302.

Filter manipulating system 300 of FIG. 7 includes an inner shaft 308 that is slidingly disposed within outer shaft lumen 306. A guidewire 330 is slidingly disposed within an inner shaft lumen 332 defined by inner shaft 308. The longitudinal movement of guidewire 330 relative to inner shaft 308 may be selectively limited by a stop mechanism 334 of filter manipulating system 300. In the embodiment of FIG. 7, stop mechanism 334 includes a gripper portion 378 of inner shaft 308 that is adapted to selectively grasp guidewire 330.

Figure 8:
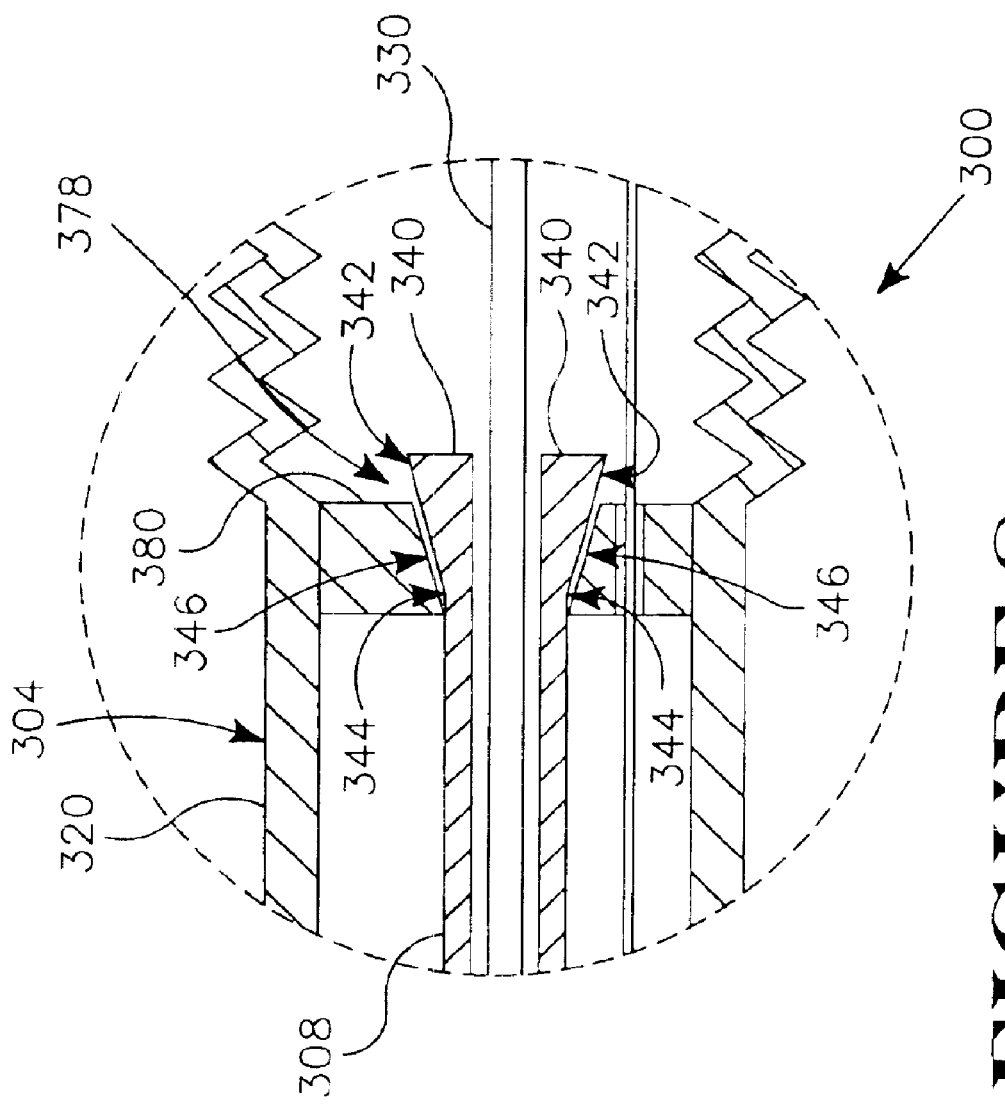
FIG. 8 is an enlarged cross-sectional view of a portion of filter manipulating system of FIG. 7.

FIG. 8 is an enlarged cross-sectional view of a portion of filter manipulating system 300 of FIG. 7. In FIG. 8, gripper portion 378 of inner shaft 308 is shown having an at rest shape. Gripper portion 378 of inner shaft 308 preferably also has a contracted shape in which gripper portion 378 of inner shaft 308 grasps guidewire 330.

In FIG. 8 it may be appreciated that gripper portion 378 of inner shaft 308 includes a plurality of jaws 340, each having a tapered portion 342 and a hinge portion 344. In may also be appreciated that stop mechanism 334 includes a closing sleeve 380 having a mating taper 346. In the embodiment of FIG. 8, closing sleeve 380 is preferably fixed to proximal portion 320 of outer shaft 304. In a preferred embodiment, relative movement between inner shaft 308 and proximal portion 320 of outer shaft 304 may be used to selectively urge jaws 340 of gripper portion 378 of inner shaft 308 against guidewire 330. In the embodiment of FIG. 8, urging inner shaft 308 proximally relative to proximal portion 320 of outer shaft 304 will preferably cause jaws 340 of gripper portion 378 of inner shaft 308 to grasp guidewire 330.

Figure 9:
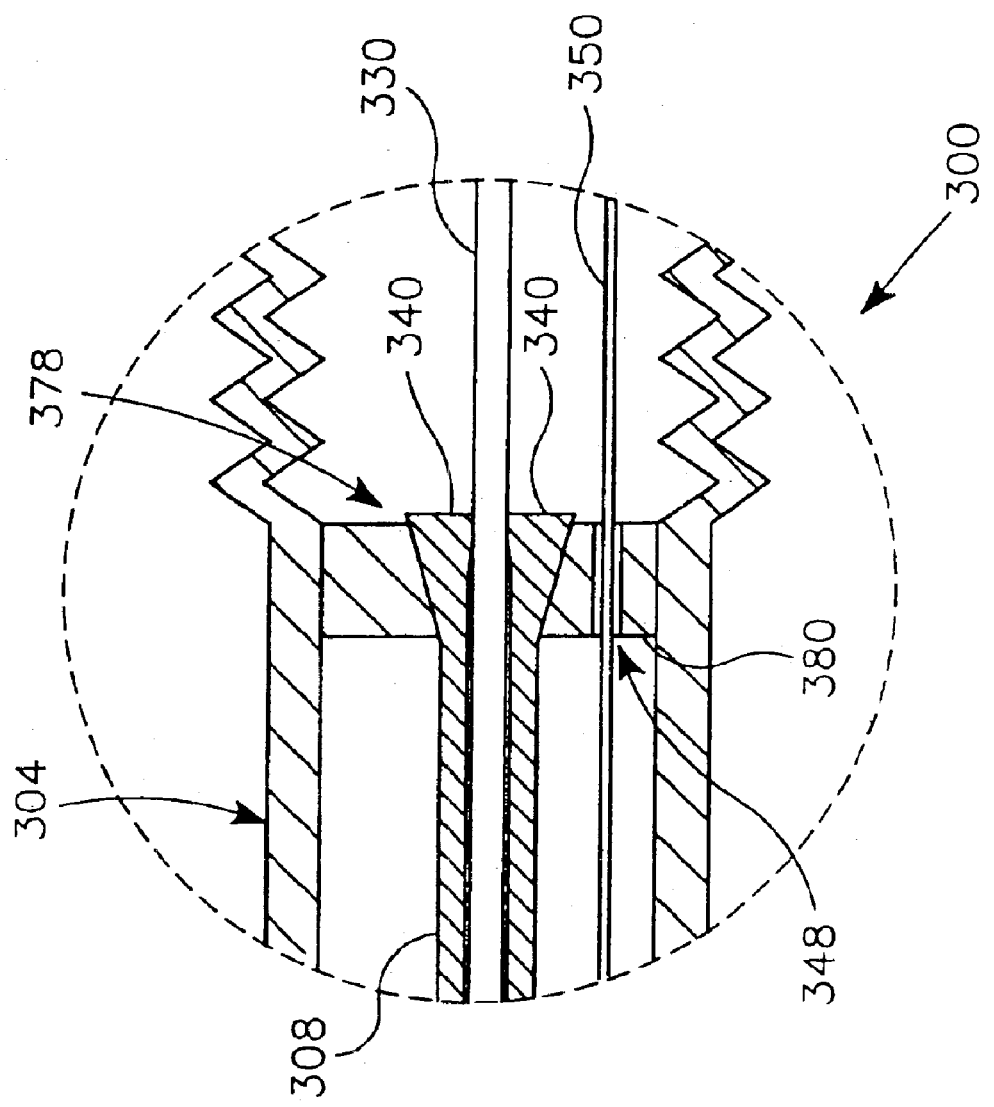
FIG. 9 is an additional enlarged cross-sectional view of the portion of filter manipulating system shown in FIG. 8.

FIG. 9 is an additional enlarged cross-sectional view of the portion of filter manipulating system 300 shown in FIG. 8. In the embodiment of FIG. 9 inner shaft 308 has been moved proximally relative to outer shaft 304 and jaws 340 of gripper portion 378 of inner shaft 308 have been urged against guidewire 330. In the embodiment of FIG. 9, gripper portion 378 of inner shaft 308 has been urged into a contracted shape.

In FIG. 9 it may also be appreciated that closing sleeve 380 defines a hole 348. An articulating rod 350 is shown extending through hole 348. Articulating rod 350 may preferably be used to selectively collapse and expand longitudinally collapsible portion 324 of outer shaft 304.

Referring again to FIG. 7, it may be appreciated that a distal end of articulating rod 350 is fixed to a ring 352. Ring 352 is preferably fixed to distal portion 322 of outer shaft 304 distally of longitudinally collapsible portion 324. The proximal end of articulating rod 350 is fixed to a slider 354. Slider 354 is disposed in sliding engagement with a hub 356 that is disposed about a proximal end 358 of outer shaft 304. In a preferred embodiment, slider 354 and articulating rod 350 may be used to selectively collapse and expand longitudinally collapsible portion 324 of outer shaft 304.

Figure 10:
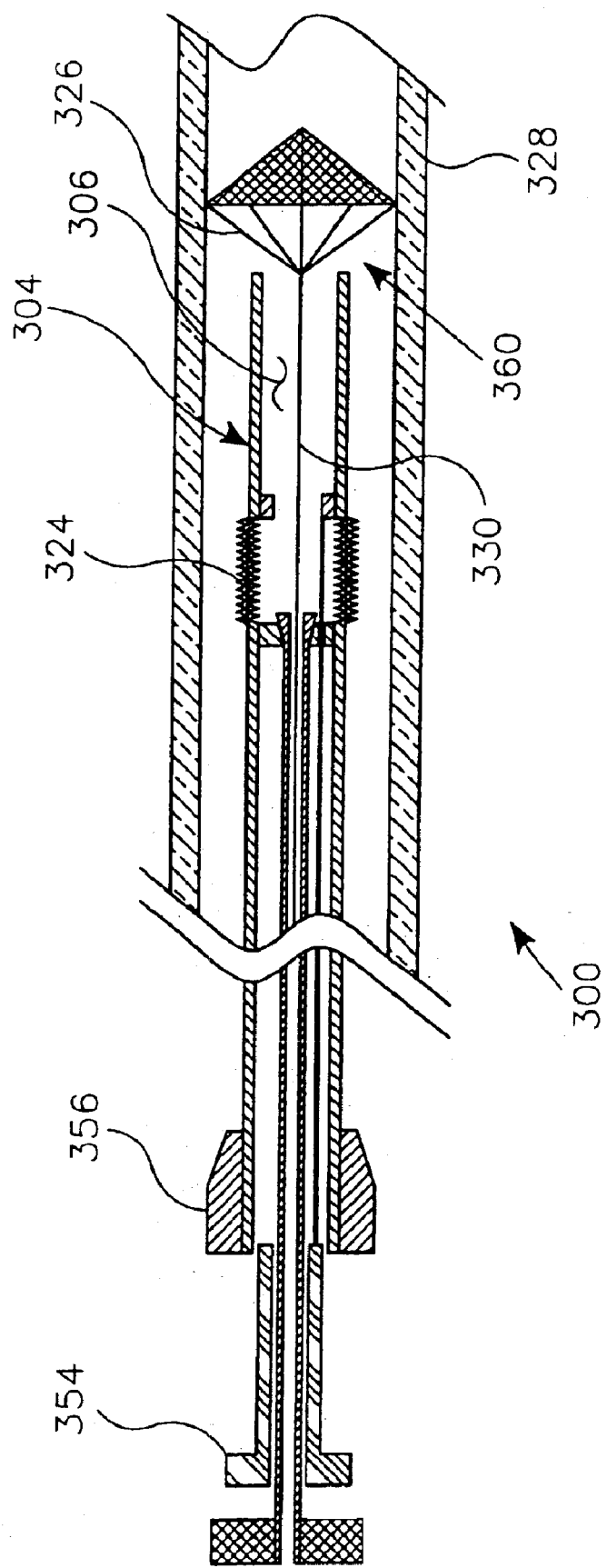
FIG. 10 is an additional partial cross-sectional view of the filter manipulating system of FIG. 7.

FIG. 10 is an additional partial cross-sectional view of the filter manipulating system 300 of FIG. 7. In the embodiment of FIG. 10, longitudinally collapsible portion 324 of outer shaft 304 has been collapsed by urging slider 354 proximally relative to hub 356. In the embodiment of FIG. 10, distal end 360 of outer shaft 304 is located proximally of filter 326 and filter 326 is disposed outside of outer shaft lumen 306. In FIG. 10 it may be appreciated that filter 326 is free to assume an expanded configuration when it is outside of outer shaft lumen 306.

Filter manipulating system 300 of FIG. 10 may preferably be used to retrieve filter 326 from blood vessel 328. For example, filter 326 may be retrieved from blood vessel 328 by selectively grasping guidewire 330 proximate filter 326 and expanding longitudinally collapsible portion 324 by pushing distally on slider 354. By expanding longitudinally collapsible portion 324, distal portion 322 of outer shaft 304 may be urged over filter 326 so that filter 326 is disposed within outer shaft lumen 306. In a preferred embodiment, filter 326 assumes an expanded configuration when it is disposed within blood vessel 328 and assumes a contracted configuration when it is disposed within outer shaft lumen 306 of catheter 302. Filter manipulating system 300 may preferably also be used to deploy a filter within a blood vessel.

Figure 11:
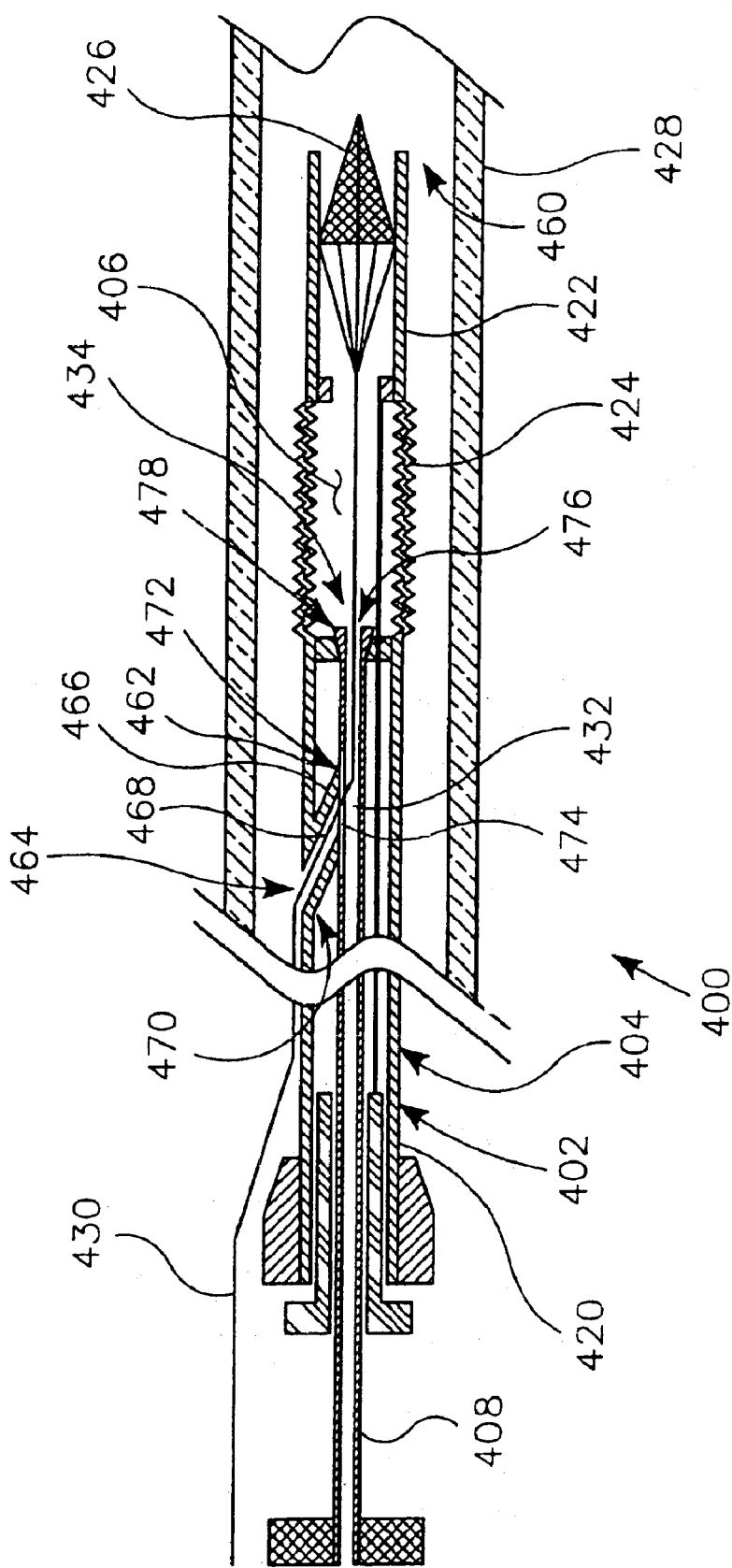
FIG. 11 is a partial cross-sectional view of a filter manipulating system in accordance with an additional exemplary embodiment of the present invention.

FIG. 11 is a partial cross-sectional view of a filter manipulating system 400 in accordance with an additional exemplary embodiment of the present invention. Filter manipulating system 400 comprises a catheter 402 including an outer shaft 404 defining an outer shaft lumen 406. Outer shaft 404 includes a proximal portion 420, a distal portion 422, and a longitudinally collapsible portion 424 disposed between proximal portion 420 and distal portion 422. A wall 462 of proximal portion 420 of outer shaft 404 defines a proximal guidewire port 464. Catheter 402 also includes a tubular member 466 having a first end 470 fixed to wall 462 of proximal portion 420 of outer shaft 404, and a second end 472 disposed within outer shaft lumen 406 proximate inner shaft 408. Tubular member 466 defines a guidewire lumen 468 that is in fluid communication with proximal guidewire port 464.

Various embodiments of proximal guidewire port 464 are possible without deviating from the spirit and scope of the present invention. For example, proximal guidewire port 464 may be defined by wall 462 of proximal portion 420 of outer shaft 404. By way of a second example, proximal guidewire port 464 may be defined by first end 470 of tubular member 466.

Filter manipulating system 400 of FIG. 11 includes an inner shaft 408 that is slidingly disposed within outer shaft lumen 406. In FIG. 11, it may be appreciated that inner shaft 408 of catheter 402 defines an inner shaft lumen 432. A wall of inner shaft 408 defines an aperture 474 that is in fluid communication with inner shaft lumen 432. In FIG. 11, a guidewire 430 is shown extending through proximal guidewire port 464, guidewire lumen 468, aperture 474, and a portion of inner shaft lumen 432.

In the embodiment of FIG. 11, the longitudinal movement of guidewire 430 relative to inner shaft 408 may be selectively limited by a stop mechanism 434 of filter manipulating system 400. Stop mechanism 434 of FIG. 11 includes a gripper portion 478 of inner shaft 408 that is adapted to selectively grasp guidewire 430. Gripper portion 478 of inner shaft 408 preferably defines a distal guidewire port 476. In FIG. 11, guidewire 430 is shown extending through distal guidewire port 476, a portion of inner shaft lumen 432, aperture 474, guidewire lumen 468, and proximal guidewire port 464.

In the embodiment of FIG. 11, distal guidewire port 476 is disposed proximally of a distal end 460 of outer shaft 404, and proximal guidewire port 464 is disposed proximally of distal guidewire port 476. In FIG. 11, it may be appreciated that distal guidewire port 476 and proximal guidewire port 464 are separated by a longitudinal distance. In a preferred embodiment, the longitudinal distance between proximal guidewire port 464 and distal guidewire port 476 is less than about 55 centimeters. In a particularly preferred embodiment, the longitudinal distance between proximal guidewire port 464 and distal guidewire port 476 is less than about 45 centimeters. In an especially preferred embodiment, the longitudinal distance between proximal guidewire port 464 and distal guidewire port 476 is less than about 35 centimeters.

In the embodiment of FIG. 11 a filter 426 of filter manipulating system 400 is disposed within a portion of outer shaft lumen 406 defined by distal portion 422 of outer shaft 404. In the embodiment of FIG. 11, filter 426 is in a contracted configuration. Catheter 402 of filter manipulating system 400 may preferably be used to deploy filter 426 within a blood vessel 428. Filter 426 may be deployed, for example, by grasping guidewire 430 proximate filter 426 and contracting longitudinally collapsible portion 424. This may cause distal portion 422 of outer shaft 404 to be drawn away from filter 426 so that filter 426 is disposed outside of outer shaft lumen 406. In a preferred embodiment, filter 426 assumes an expanded configuration when it is disposed outside of outer shaft lumen 406 and assumes a contracted configuration when it is disposed within outer shaft lumen 406 of catheter 402. Filter manipulating system 400 may also preferably be used to retrieve a filter that is disposed within a blood vessel.

Figure 12:
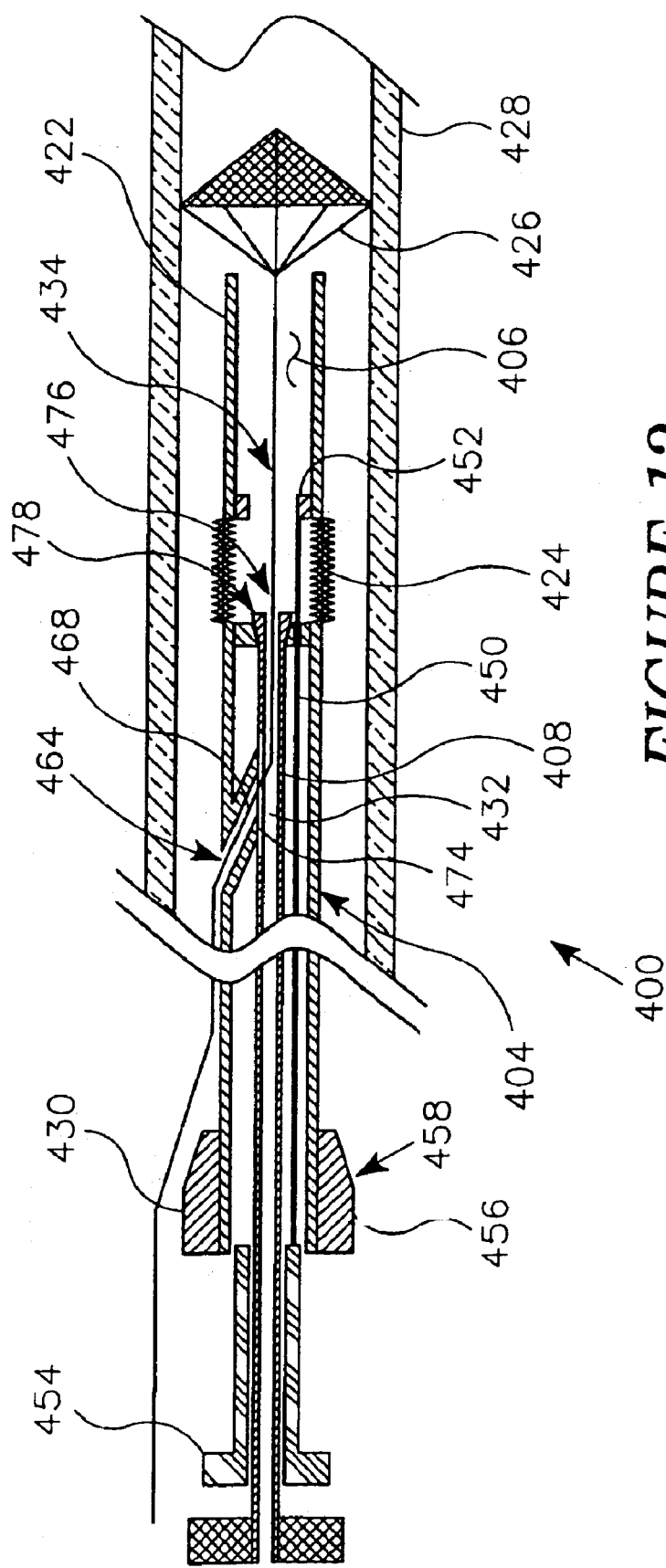
FIG. 12 is an additional partial cross-sectional view of the filter manipulating system of FIG. 11.

FIG. 12 is an additional partial cross-sectional view of the filter manipulating system 400 of FIG. 11. In the embodiment of FIG. 12, filter 426 is disposed within blood vessel 428. Filter 426 may be retrieved, for example, by grasping guidewire 430 with gripper portion 478 of inner shaft 408 and expanding longitudinally collapsible portion 424 of outer shaft 404. In a preferred embodiment, filter 426 assumes an expanded configuration when it is disposed within blood vessel 428 and assumes a contracted configuration when it is disposed within outer shaft lumen 406 of catheter 402.

In FIG. 12, it may be appreciated that an articulating rod 450 is disposed within outer shaft lumen 406 defined by outer shaft 404. A distal end of articulating rod 450 is fixed to a ring 452. Ring 452 is preferably fixed to distal portion 422 of outer shaft 404 distally of longitudinally collapsible portion 424. The proximal end of articulating rod 450 is fixed to a slider 454. Slider 454 is disposed in sliding engagement with a hub 456 that is disposed about a proximal end 458 of outer shaft 404. In a preferred embodiment, slider 454 and articulating rod 450 may be used to selectively collapse longitudinally collapsible portion 424 of outer shaft 404.

A distal end of a guidewire 430 is shown fixed to filter 426. In the embodiment of FIG. 12, guidewire 430 extends through distal guidewire port 476, a portion of inner shaft lumen 432, aperture 474, guidewire lumen 468, and proximal guidewire port 464. Stop mechanism 434 may preferably be used to selectively grasp guidewire 430 at a location proximate filter 426.

Figure 13:
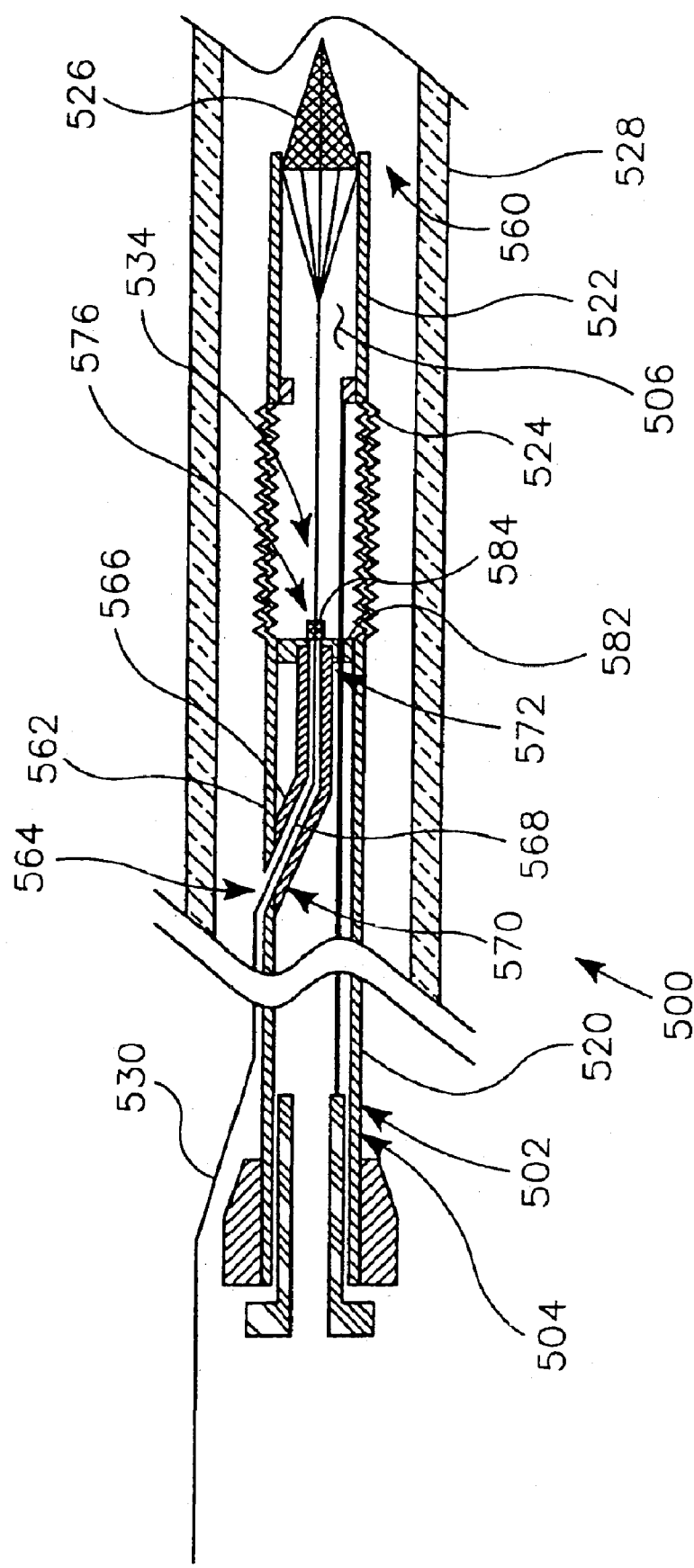
FIG. 13 is a partial cross-sectional view of a filter manipulating system in accordance with an additional exemplary embodiment of the present invention.

FIG. 13 is a partial cross-sectional view of a filter manipulating system 500 in accordance with an additional exemplary embodiment of the present invention. Filter manipulating system 500 comprises a catheter 502 including an outer shaft 504 defining an outer shaft lumen 506. Outer shaft 504 includes a proximal portion 520, a distal portion 522, and a longitudinally collapsible portion 524 disposed between proximal portion 520 and distal portion 522. A wall 562 of proximal portion 520 of outer shaft 504 defines a proximal guidewire port 564. Catheter 502 also includes a tubular member 566 having a first end 570 fixed to wall 562 of proximal portion 520 of outer shaft 504, and a second end 572 preferably fixed to a stop member 582. Stop member 582 defines a distal guidewire port 576. Tubular member 566 defines a guidewire lumen 568 that is in fluid communication with distal guidewire port 576 and proximal guidewire port 564. In FIG. 13, guidewire 530 is shown extending through distal guidewire port 576, guidewire lumen 568, and proximal guidewire port 564.

In the embodiment of FIG. 13, longitudinal movement of guidewire 530 relative to stop member 582 may be selectively limited by a stop mechanism 534 of filter manipulating system 500. Stop mechanism 534 of FIG. 13 includes stop member 582 and a stop 584 that is preferably fixed to guidewire 530. In the embodiment of FIG. 13, stop 584 comprises a radial enlargement. In a preferred embodiment, stop 584 has an outer radial extent of about 0.014 inches and guidewire 530 has an outer radial extent of about 0.010 inches. In FIG. 13, stop 584 is shown seated against stop member 582.

In the embodiment of FIG. 13, distal guidewire port 576 is disposed proximally of a distal end 560 of outer shaft 504, and proximal guidewire port 564 is disposed proximally of distal guidewire port 576. In FIG. 13, it may be appreciated that distal guidewire port 576 and proximal guidewire port 564 are separated by a longitudinal distance. In a preferred embodiment, the longitudinal distance between proximal guidewire port 564 and distal guidewire port 576 is less than about 55 centimeters. In a particularly preferred embodiment, the longitudinal distance between proximal guidewire port 564 and distal guidewire port 576 is less than about 45 centimeters. In an especially preferred embodiment, the longitudinal distance between proximal guidewire port 564 and distal guidewire port 576 is less than about 35 centimeters.

In the embodiment of FIG. 13 a filter 526 of filter manipulating system 500 is disposed within a portion of outer shaft lumen 506 defined by distal portion 522 of outer shaft 504. In the embodiment of FIG. 13, filter 526 is in a contracted configuration. Catheter 502 of filter manipulating system 500 may preferably be used to deploy filter 526 within a blood vessel 528. Filter 526 may be deployed, for example, by contracting longitudinally collapsible portion 524. This may cause distal portion 522 of outer shaft 504 to be drawn away from filter 526 so that filter 526 is disposed outside of outer shaft lumen 506. In a preferred embodiment, filter 526 assumes an expanded configuration when it is disposed outside of outer shaft lumen 506 and assumes a contracted configuration when it is disposed within outer shaft lumen 506 of catheter 502. Filter manipulating system 500 may also preferably be used to retrieve a filter that is disposed within a blood vessel.

Figure 14:
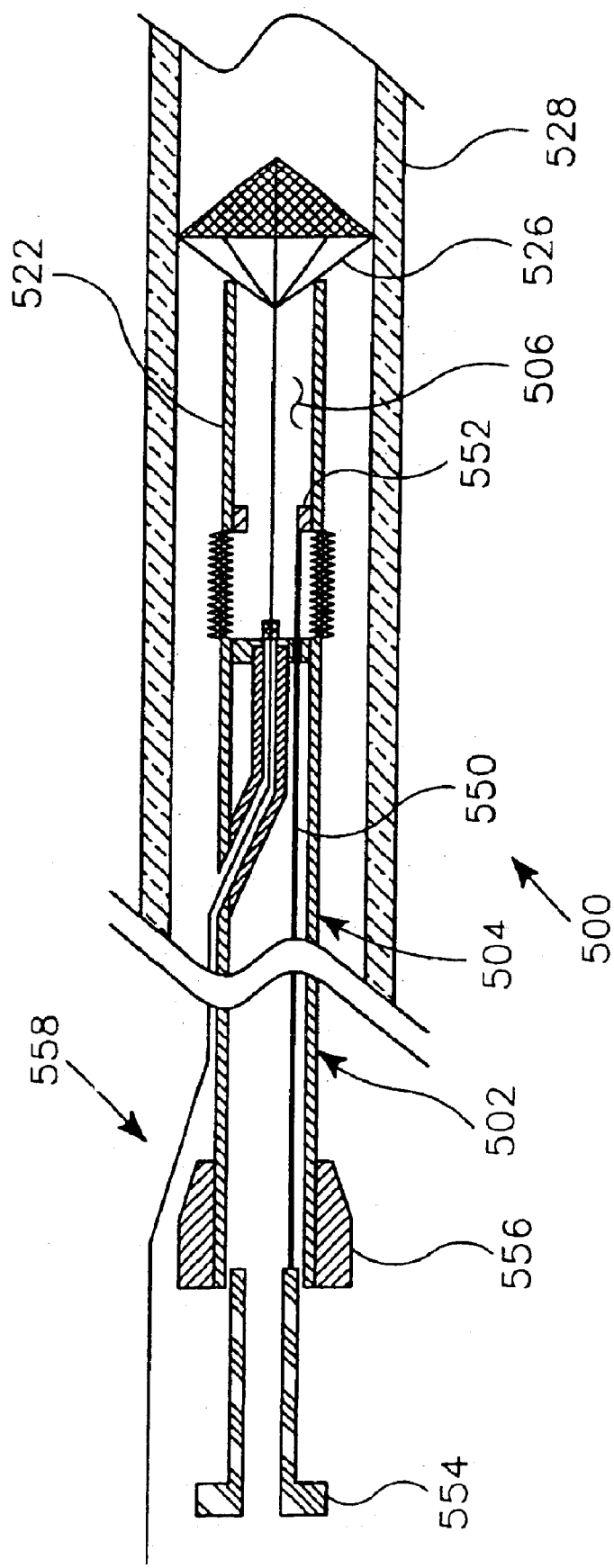
FIG. 14 is an additional partial cross-sectional view of the filter manipulating system of FIG. 13.

FIG. 14 is an additional partial cross-sectional view of the filter manipulating system 500 of FIG. 13. In the embodiment of FIG. 14, filter 526 is disposed within blood vessel 528. In a preferred embodiment, filter 526 assumes an expanded configuration when it is disposed within blood vessel 528 and assumes a contracted configuration when it is disposed within outer shaft lumen 506 of catheter 502.

In FIG. 14, it may be appreciated that an articulating rod 550 is disposed within outer shaft lumen 506 defined by outer shaft 504. A distal end of articulating rod 550 is fixed to a ring 552. Ring 552 is preferably fixed to distal portion 522 of outer shaft 504 distally of longitudinally collapsible portion 524. The proximal end of articulating rod 550 is fixed to a slider 554. Slider 554 is disposed in sliding engagement with a hub 556 that is disposed about a proximal end 558 of outer shaft 504. In a preferred embodiment, slider 554 and articulating rod 550 may be used to selectively collapse longitudinally collapsible portion 524 of outer shaft 504.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A system for manipulating a filter fixed to a guidewire disposed within a blood vessel, comprising:

an outer shaft having a proximal portion, a distal portion, and a longitudinally collapsible portion disposed between the proximal portion and the distal portion, said outer shaft defining an outer shaft lumen; and a stop mechanism adapted to selectively limit longitudinal movement of the guidewire relative to the outer shaft, the stop mechanism being positioned within the outer shaft lumen, wherein the stop mechanism is configured such that relative axial movement between the inner shaft and the outer shaft urges the stop mechanism to assume a deflected shape.

2. A system for manipulating a filter fixed to a guidewire disposed within a blood vessel, comprising:

an outer shaft having a proximal portion, a distal portion, and a longitudinally collapsible portion disposed between the proximal portion and the distal portion, said outer shaft defining an outer shaft lumen; and a stop mechanism adapted to selectively limit longitudinal movement of the guidewire relative to the outer shaft, the stop mechanism being positioned within the outer shaft lumen, wherein the stop mechanism includes a stop member defining a distal guidewire port.

3. A system for manipulating a filter fixed to a guidewire disposed within a blood vessel, comprising:

an outer shaft having a proximal portion, a distal portion, and a longitudinally collapsible portion disposed between the proximal portion and the distal portion, said outer shaft defining an outer shaft lumen; and a stop mechanism adapted to selectively limit longitudinal movement of the guidewire relative to the outer shaft, the stop mechanism being positioned within the outer shaft lumen, wherein the stop member includes a stop member comprising a collet.

4. A system for manipulating a filter fixed to a guidewire disposed within a blood vessel, comprising:

an outer shaft having a proximal portion, a distal portion, and a longitudinally collapsible portion disposed between the proximal portion and the distal portion, said outer shaft defining an outer shaft lumen; and a stop mechanism adapted to selectively limit longitudinal movement of the guidewire relative to the outer shaft, the stop mechanism being positioned within the outer shaft lumen, wherein the stop mechanism includes a stop member including a distal mating surface.

5. A system for manipulating a filter fixed to a guidewire disposed within a blood vessel, comprising:

an outer shaft having a proximal portion, a distal portion, and a longitudinally collapsible portion disposed between the proximal portion and the distal portion, said outer shaft defining an outer shaft lumen; and a stop mechanism adapted to selectively limit longitudinal movement of the guidewire relative to the outer shaft, the stop mechanism being positioned within the outer shaft lumen, wherein the stop mechanism includes a stop fixed to the guidewire and wherein the stop includes a proximal mating surface.

6. A system for manipulating a filter fixed to a guidewire disposed within a blood vessel, comprising:

an outer shaft having a proximal portion, a distal portion, and a longitudinally collapsible portion disposed between the proximal portion and the distal portion, said outer shaft defining an outer shaft lumen; and a stop mechanism adapted to selectively limit longitudinal movement of the guidewire relative to the outer shaft, the stop mechanism being positioned within the outer shaft lumen, further including an articulating member having a proximal portion and a distal portion, the articulating member configured to engage the longitudinally collapsible portion of said outer shaft between a collapsed position and an expanded position.

7. The system of claim 6, wherein the filter assumes a deployed position when the longitudinally collapsible portion is engaged in the collapsed position, and a contracted position when the longitudinally collapsible portion is engaged in the expanded position.

8. The system of claim 6, wherein the proximal portion of said articulating member is coupled to a slider.

9. The system of claim 6, wherein the distal portion of said articulating member is coupled to a ring secured to the distal portion of the outer shaft.

10. A system for manipulating a filter fixed to a guidewire disposed within a blood vessel, comprising:

an outer shaft having a proximal portion, a distal portion, and a longitudinally collapsible portion disposed between the proximal portion and the distal portion, said outer shaft defining an outer shaft lumen; and a stop mechanism adapted to selectively limit longitudinal movement of the guidewire relative to the outer shaft, the stop mechanism being positioned within the outer shaft lumen, further including a proximal guidewire port extending through a wall defined by the outer shaft.

11. A system for manipulating a filter fixed to a guidewire disposed within a blood vessel, comprising:

an outer shaft having a proximal portion, a distal portion, and a longitudinally collapsible portion disposed between the proximal portion and the distal portion, said outer shaft defining an outer shaft lumen;

an articulating member having a proximal portion and a distal portion, the articulating member configured to engage the longitudinally collapsible portion between a collapsed position and an expanded position; and a stop mechanism adapted to selectively limit longitudinal movement of the guidewire relative to the outer shaft, the stop mechanism being positioned within the outer shaft lumen, further including an inner shaft slidably disposed within the outer shaft lumen, said inner shaft defining an inner shaft lumen configured to slidably receive the guidewire, wherein the stop mechanism is configured such that relative axial movement between the inner shaft and the outer shaft urges the stop mechanism to assume a deflected shape.

12. A system for manipulating a filter fixed to a guidewire disposed within a blood vessel, comprising:

an outer shaft having a proximal portion, a distal portion, and a longitudinally collapsible portion disposed between the proximal portion and the distal portion, said outer shaft defining an outer shaft lumen;

an articulating member having a proximal portion and a distal portion, the articulating member configured to engage the longitudinally collapsible portion between a collapsed position and an expanded position; and a stop mechanism adapted to selectively limit longitudinal movement of the guidewire relative to the outer shaft, the stop mechanism being positioned within the outer shaft lumen, wherein the stop mechanism includes a stop member coupled to the outer shaft that defines a distal guidewire port.

13. A system for manipulating a filter fixed to a guidewire disposed within a blood vessel, comprising:

an outer shaft having a proximal portion, a distal portion, and a longitudinally collapsible portion disposed between the proximal portion and the distal portion, said outer shaft defining an outer shaft lumen;

an articulating member having a proximal portion and a distal portion, the articulating member configured to engage the longitudinally collapsible portion between a collapsed position and an expanded position; and a stop mechanism adapted to selectively limit longitudinal movement of the guidewire relative to the outer shaft, the stop mechanism being positioned within the outer shaft lumen, wherein the stop mechanism includes a stop member coupled to the outer shaft that comprises a collet.

14. A system for manipulating a filter fixed to a guidewire disposed within a blood vessel, comprising:

an outer shaft having proximal portion, a distal portion, and a longitudinally collapsible portion disposed between the proximal portion and the distal portion, said outer shaft defining an outer shaft lumen;

an articulating member having a proximal portion and a distal portion, the articulating member configured to engage the longitudinally collapsible portion between a collapsed position and an expanded position; and a stop mechanism adapted to selectively limit longitudinal movement of the guidewire relative to the outer shaft, the stop mechanism being positioned within the outer shaft lumen, wherein the stop mechanism includes a stop member coupled to the outer shaft that includes a distal mating surface.

* * * * *